US009145407B2

(12) United States Patent
Markworth et al.

(10) Patent No.: US 9,145,407 B2
(45) Date of Patent: *Sep. 29, 2015

(54) SULFONAMIDE COMPOUNDS

(75) Inventors: Christopher John Markworth, Durham, NC (US); Brian Edward Marron, Durham, NC (US); David James Rawson, Sandwich (GB); Robert Ian Storer, Sandwich (GB); Nigel Alan Swain, Sandwich (GB); Christopher William West, Durham, NC (US); Shulan Zhou, Durham, NC (US)

(73) Assignees: Pfizer Limited, Sandwich (GB); Icagen, Inc., Durham, NC (US)

( * ) Notice: Subject to any disclaimer, the term of this patent is extended or adjusted under 35 U.S.C. 154(b) by 234 days.

This patent is subject to a terminal disclaimer.

(21) Appl. No.: 13/808,625

(22) PCT Filed: Jun. 28, 2011

(86) PCT No.: PCT/IB2011/052840
§ 371 (c)(1),
(2), (4) Date: Jan. 7, 2013

(87) PCT Pub. No.: WO2012/004706
PCT Pub. Date: Jan. 12, 2012

(65) Prior Publication Data
US 2013/0109667 A1    May 2, 2013

Related U.S. Application Data

(60) Provisional application No. 61/362,904, filed on Jul. 9, 2010.

(51) Int. Cl.
| A61K 31/506 | (2006.01) |
| C07D 401/12 | (2006.01) |
| C07D 417/12 | (2006.01) |
| C07D 417/14 | (2006.01) |
| A61K 31/427 | (2006.01) |
| A61K 31/433 | (2006.01) |
| A61K 31/4439 | (2006.01) |
| A61K 31/501 | (2006.01) |

(52) U.S. Cl.
CPC ............ *C07D 417/14* (2013.01); *A61K 31/427* (2013.01); *A61K 31/433* (2013.01); *A61K 31/4439* (2013.01); *A61K 31/501* (2013.01); *A61K 31/506* (2013.01); *C07D 401/12* (2013.01); *C07D 417/12* (2013.01)

(58) Field of Classification Search
CPC ............................ C07D 401/12; C07D 417/12
See application file for complete search history.

(56) References Cited

U.S. PATENT DOCUMENTS

| 3,905,971 | A | 9/1975 | Miller |
| 4,782,056 | A | 11/1988 | Rosner et al. |
| 4,945,090 | A | 7/1990 | Schmiechen et al. |
| 5,389,635 | A | 2/1995 | Olson |
| 6,087,392 | A | 7/2000 | Reiter |
| 6,110,964 | A | 8/2000 | Robinson |
| 6,197,810 | B1 | 3/2001 | Reiter |
| 6,214,870 | B1 | 4/2001 | McClure et al. |
| 6,342,521 | B1 | 1/2002 | Reiter |
| 8,188,277 | B2 | 5/2012 | Fukushima et al. |
| 8,410,276 | B2 | 4/2013 | Takaoka |
| 8,592,629 | B2 * | 11/2013 | Bell et al. .................. 564/99 |
| 2001/0046989 | A1 | 11/2001 | Levin et al. |
| 2003/0158186 | A1 | 8/2003 | Malik et al. |
| 2004/0110743 | A1 | 6/2004 | Miyamato et al. |
| 2004/0214870 | A1 | 10/2004 | Xin et al. |
| 2005/0009871 | A1 | 1/2005 | Ramesh et al. |
| 2005/0107364 | A1 | 5/2005 | Hutchinson et al. |
| 2005/0282818 | A1 | 12/2005 | Ramesh et al. |
| 2006/0183745 | A1 | 8/2006 | Bo et al. |
| 2007/0135431 | A1 | 6/2007 | Smith et al. |
| 2007/0167497 | A1 | 7/2007 | Nambu et al. |
| 2008/0103129 | A1 | 5/2008 | Zhang et al. |
| 2008/0242656 | A1 | 10/2008 | Fryer et al. |
| 2008/0293706 | A1 | 11/2008 | Chaudhari et al. |
| 2009/0143358 | A1 | 6/2009 | Marron et al. |
| 2010/0056528 | A1 | 3/2010 | Yacovan et al. |
| 2010/0197655 | A1 | 8/2010 | Beaudoin et al. |
| 2011/0077269 | A1 | 3/2011 | Martinborough |
| 2012/0010182 | A1 | 1/2012 | Brown et al. |
| 2012/0010183 | A1 | 1/2012 | Bell et al. |
| 2012/0010207 | A1 | 1/2012 | Bell |
| 2013/0109696 | A1 | 5/2013 | Greener et al. |

(Continued)

FOREIGN PATENT DOCUMENTS

| EP | 0532239 A1 | 3/1993 |
| EP | 0569193 A1 | 11/1993 |

(Continued)

OTHER PUBLICATIONS

Hong, Guizhu, et al., PPARγ activation enhances cell surface ENaCα via up-regulation of SGK1 in human collecting duct cells, The FASEB Journal, Oct. 2003, pp. 1966-1968, vol. 17.
Payne, J., et al., "Identification of KD5170: A novel mercaptoketone based histone deacetylase inhibitor", Bioorganic and Medicinal Chemistry Letters, 2008, pp. 6093-6096, vol. 18, No. 23.
RN 1031058-98-6 chemical Abstracts Registry database, Jun. 26, 2008, Aurora Fine Chemicals.
Kharul, R., et al. "Efficient Synthesis of Structurally Novel Diary Ethers by Regioselective Functionalization", Synthetic Communications, 2008, pp. 4282-4294, 38(23).
Ohta, B. "Studies on Chemotherapeutics, XVII. Intramolecular Rearrangement of p-Hydroxy-benzenes ulfonamide Derivatives", Yakugaku Zassi—(Series), 1951, pp. 315-318, vol. 71.

(Continued)

*Primary Examiner* — Brian McDowell
(74) *Attorney, Agent, or Firm* — J. Michael Dixon

(57) ABSTRACT

The invention relates to new sulfonamide Nav1.7 inhibitors and pharmaceutically acceptable salts thereof, to their use in medicine, to compositions containing them, to processes for their preparation and to intermediates used in such processes. Nav 1.7 inhibitors are potentially useful in the treatment of a wide range of disorders, particularly pain.

10 Claims, No Drawings

(56) References Cited

U.S. PATENT DOCUMENTS

| | | |
|---|---|---|
| 2013/0109701 A1 | 5/2013 | Brown et al. |
| 2013/0109708 A1 | 5/2013 | Brown et al. |
| 2013/0116285 A1 | 5/2013 | Bell et al. |

FOREIGN PATENT DOCUMENTS

| | | | |
|---|---|---|---|
| EP | 1088819 A2 | 4/2001 | |
| EP | 1201238 A1 | 2/2002 | |
| GB | 2263635 A | 8/1993 | |
| WO | 9427979 A1 | 12/1994 | |
| WO | 9746556 A1 | 12/1997 | |
| WO | 9942462 A1 | 8/1999 | |
| WO | 0156989 A2 | 8/2001 | |
| WO | 02051831 A1 | 7/2002 | |
| WO | 03022277 A1 | 3/2003 | |
| WO | 03048159 A1 | 6/2003 | |
| WO | 2004002481 A1 | 1/2004 | |
| WO | 2004014370 A2 | 2/2004 | |
| WO | 2004084898 A1 | 10/2004 | |
| WO | 2004103980 A1 | 12/2004 | |
| WO | 2005000309 A2 | 1/2005 | |
| WO | 2005007621 A2 | 1/2005 | |
| WO | 2005013914 A2 | 2/2005 | |
| WO | 2005054176 A1 | 6/2005 | |
| WO | 2005116026 A1 | 12/2005 | |
| WO | 2006051270 A1 | 5/2006 | |
| WO | 2006060762 A2 | 6/2006 | |
| WO | 2006076644 A2 | 7/2006 | |
| WO | 2007002584 A1 | 1/2007 | |
| WO | 2007002635 A2 | 1/2007 | |
| WO | 2007039171 A1 | 4/2007 | |
| WO | 2007076034 A2 | 7/2007 | |
| WO | 2007118859 A1 | 10/2007 | |
| WO | 2007125351 A1 | 11/2007 | |
| WO | 2008002490 A2 | 1/2008 | |
| WO | 2008046216 A1 | 4/2008 | |
| WO | 2008050200 A1 | 5/2008 | |
| WO | 2008057280 A1 | 5/2008 | |
| WO | 2008118758 A1 | 5/2008 | |
| WO | 2008079291 A1 | 7/2008 | |
| WO | 2008137027 A2 | 11/2008 | |
| WO | 2009011850 A2 | 1/2009 | |
| WO | 2009012242 A1 | 1/2009 | |
| WO | 2009017719 A2 | 2/2009 | |
| WO | 2009065131 A1 | 5/2009 | |
| WO | 2009127822 A2 | 10/2009 | |
| WO | 2009129267 A2 | 10/2009 | |

OTHER PUBLICATIONS

Reiter, L. et al. "Pyran-containing sulfonamide hydroxamic acids: potent MMP inhibitors that spare MMP-1", Bioorganic and Medicinal Chemistry Letters, 2004, pp. 3389-3395, vol. 14, No. 13.

Silverman, Richard B. The Organic Chemistry of Drug Design and Drug Action. 2nd Ed., 2004, pp. 29-32, Elsevier, Burlington, MA.

* cited by examiner

SULFONAMIDE COMPOUNDS

CROSS REFERENCE

This application is the National Stage Application of International Patent Application No. PCT/IB2011/052840, filed Jun. 28, 2011, which claims priority to U.S. Provisional Patent Application No. 61/362,904, filed on Jul. 9, 2010.

The invention relates to sulfonamide derivatives, to their use in medicine, to compositions containing them, to processes for their preparation and to intermediates used in such processes.

Voltage-gated sodium channels are found in all excitable cells including myocytes of muscle and neurons of the central and peripheral nervous system. In neuronal cells, sodium channels are primarily responsible for generating the rapid upstroke of the action potential. In this manner sodium channels are essential to the initiation and propagation of electrical signals in the nervous system. Proper and appropriate function of sodium channels is therefore necessary for normal function of the neuron. Consequently, aberrant sodium channel function is thought to underlie a variety of medical disorders (see Hubner C A, Jentsch T J, *Hum. Mol. Genet.*, 11(20): 2435-45 (2002) for a general review of inherited ion channel disorders) including epilepsy (Yogeeswari et al., *Curr. Drug Targets*, 5(7): 589-602 (2004)), arrhythmia (Noble D., *Proc. Natl. Acad. Sci. USA*, 99(9): 5755-6 (2002)) myotonia (Cannon, S C, *Kidney Int.* 57(3): 772-9 (2000)), and pain (Wood, J N et al., *J. Neurobiol.*, 61(1): 55-71 (2004)).

There are currently at least nine known members of the family of voltage-gated sodium channel (VGSC) alpha subunits. Names for this family include SCNx, SCNAx, and Na$_v$x.x. The VGSC family has been phylogenetically divided into two subfamilies Na$_v$1.x (all but SCN6A) and Na$_v$2.x (SCN6A). The Nav1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

The Na$_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA*, 94(4): 1527-1532 (1997)).

An increasing body of evidence suggests that Na$_v$1.7 may play a key role in various pain states, including acute, inflammatory and/or neuropathic pain. Deletion of the SCN9A gene in nociceptive neurons of mice led to a reduction in mechanical and thermal pain thresholds and reduction or abolition of inflammatory pain responses (Nassar et al., *Proc Natl Acad Sci USA*, 101(34): 12706-11 (2004)). In humans, Na$_v$1.7 protein has been shown to accumulate in neuromas, particularly painful neuromas (Kretschmer et al., *Acta. Neurochir.* (*Wien*), 144(8): 803-10 (2002)). Gain of function mutations of Na$_v$1.7, both familial and sporadic, have been linked to primary erythermalgia, a disease characterized by burning pain and inflammation of the extremities (Yang et al., *J. Med. Genet.*, 41(3): 171-4 (2004), and paroxysmal extreme pain disorder (Waxman, S G *Neurology.* 7; 69(6): 505-7 (2007)). Congruent with this observation is the report that the non-selective sodium channel blockers lidocaine and mexiletine can provide symptomatic relief in cases of familial erythermalgia (Legroux-Crepel et al., *Ann. Dermatol Venereol.*, 130: 429-433) and carbamazepine is effective in reducing the number and severity of attacks in PEPD (Fertleman et al, *Neuron.*; 52(5):767-74 (2006). Further evidence of the role of Nav1.7 in pain is found in the phenotype of loss of function mutations of the SCN9A gene. Cox and colleagues (*Nature*, 444(7121):894-8 (2006)) were the first to report an association between loss-of-function mutations of SNC9A and congenital indifference to pain (CIP), a rare autosomal recessive disorder characterized by a complete indifference or insensitivity to painful stimuli. Subsequent studies have revealed a number of different mutations that result in a loss of function of the SCN9A gene and the CIP phenotype (Goldberg et al, *Clin Genet.*; 71(4): 311-9 (2007), Ahmad et al, *Hum Mol. Genet.* 1; 16(17): 2114-21 (2007)).

Nav 1.7 inhibitors are therefore potentially useful in the treatment of a wide range of disorders, particularly pain, including: acute pain; chronic pain; neuropathic pain; inflammatory pain; visceral pain; nociceptive pain including post-surgical pain; and mixed pain types involving the viscera, gastrointestinal tract, cranial structures, musculoskeletal system, spine, urogenital system, cardiovascular system and CNS, including cancer pain, back and orofacial pain.

Certain inhibitors of voltage gated sodium channels useful in the treatment of pain are known. Thus WO-A-2005/013914 discloses heteroarylamino sulfonylphenyl derivatives, WO-A-2008/118758 aryl sulphonamides and WO-A-2009/012242 N-thiazolyl benzenesulfonamides.

There is, however, an ongoing need to provide new Na$_v$1.7 inhibitors that are good drug candidates.

Preferably compounds are selective Nav1.7 channel inhibitors. That is, preferred compounds show an affinity for the Nav1.7 channel over other Nav channels. In particular, they should show an affinity for the Nav1.7 channel which is greater than their affinity for Nav1.5 channels. Advantageously, compounds should show little or no affinity for the Nav1.5 channel.

Selectivity for the Nav1.7 channel over Nav1.5 may potentially lead to one or more improvements in side-effect profile. Without wishing to be bound by theory, such selectivity is thought to reduce any cardiovascular side effects which may be associated with affinity for the Nav1.5 channel. Preferably compounds demonstrate a selectivity of 10-fold, more preferably 30-fold, most preferably 100-fold, for the Nav 1.7 channel when compared to their selectivity for the Nav1.5 channel whilst maintaining good potency for the Nav1.7 channel.

Furthermore, preferred compounds should have one or more of the following properties: be well absorbed from the gastrointestinal tract; be metabolically stable; have a good metabolic profile, in particular with respect to the toxicity or allergenicity of any metabolites formed; or possess favourable pharmacokinetic properties whilst still retaining their activity profile as Nav1.7 channel inhibitors. They should be non-toxic and demonstrate few side-effects. Ideal drug candidates should exist in a physical form that is stable, non-hygroscopic and easily formulated.

We have now found new sulphonamide Nav1.7 inhibitors.

According to a first aspect of the invention there is provided a compound selected from the following list:

5-Chloro-4-[4-chloro-2-(2-piperazin-1-ylpyrimidin-4-yl) phenoxy]-2-fluoro-N-1,3-thiazol-4-ylbenzenesulfonamide;

5-Chloro-4-[4-chloro-2-(2-piperazin-1-ylpyrimidin-4-yl) phenoxy]-2-fluoro-N-1,3,4-thiadiazol-2-ylbenzenesulfonamide;

5-Chloro-2-fluoro-4-[5-fluoro-2-pyridazin-4-yl-4-(trifluoromethyl)phenoxy]-N-1,3-thiazol-4-ylbenzenesulfonamide;

5-Chloro-2-fluoro-4-[4-fluoro-2-pyridazin-4-yl-5-(trifluoromethyl)phenoxy]-N-1,3-thiazol-4-ylbenzenesulfonamide;

4-[2-(2-Aminopyridin-4-yl)-4-chlorophenoxy]-5-chloro-2-fluoro-N-(5-fluoropyrimidin-2-yl)benzenesulfonamide;

4-[2-(2-Aminopyridin-4-yl)-4-(trifluoromethyl)phenoxy]-5-chloro-2-fluoro-N-(5-fluoropyrimidin-2-yl)benzenesulfonamide;

4-[2-(2-Aminopyridin-4-yl)-4-fluorophenoxy]-5-chloro-2-fluoro-N-1,3-thiazol-4-ylbenzenesulfonamide;

4-[2-(3-Amino-1H-pyrazol-4-yl)-4-(trifluoromethoxy)phenoxy]-5-chloro-2-fluoro-N-1,3-thiazol-4-ylbenzenesulfonamide;

4-[2-(2-Aminopyridin-4-yl)-4-chlorophenoxy]-3-chloro-N-1,3,4-thiadiazol-2-ylbenzenesulfonamide;

4-[2-(2-Aminopyridin-4-yl)-4-chlorophenoxy]-5-chloro-2-fluoro-N-1,3-thiazol-4-ylbenzenesulfonamide;

4-[2-(5-Amino-1H-pyrazol-4-yl)-4-fluorophenoxy]-5-chloro-2-fluoro-N-1,3-thiazol-4-ylbenzenesulfonamide;

5-Chloro-2-fluoro-4-[2-pyridazin-4-yl-4-(trifluoromethoxy)phenoxy]-N-1,3-thiazol-4-ylbenzenesulfonamide;

4-[2-(1-Azetidin-3-yl-1H-pyrazol-5-yl)-5-chloro-2-fluoro-4-(trifluoromethyl)phenoxy]-N-1,3,4-thiadiazol-5-ylbenzenesulfonamide;

5-Chloro-2-fluoro-4-{4-trifluoromethyl-2-[1-(1-methylazetidin-3-yl)-1H-pyrazol-5-yl]phenoxy}-N-1,3,4-thiadiazol-ylbenzenesulfonamide;

3-Cyano-4-[2-(3-methylpyridazin-4-yl)-4-(trifluoromethyl)phenoxy]-N-1,2,4-thiadiazol-5-ylbenzenesulfonamide;

3-Methyl-4-[2-pyridazin-4-yl-4-(trifluoromethyl)phenoxy]-N-1,2,4-thiadiazol-5-ylbenzenesulfonamide;

4-[4-chloro-2-(2-piperazin-1-ylpyrimidin-4-yl)phenoxy]-2,5-difluoro-N-1,3-thiazol-4-ylbenzenesulfonamide;

4-[4-chloro-2-(2-piperazin-1-ylpyridin-4-yl)phenoxy]-2,5-difluoro-N-pyrimidin-2-ylbenzenesulfonamide;

4-[4-chloro-2-(2-piperazin-1-ylpyridin-4-yl)phenoxy]-3-cyano-N-pyrimidin-2-ylbenzenesulfonamide;

4-[4-chloro-2-(2-piperazin-1-ylpyrimidin-4-yl)phenoxy]-3-cyano-N-pyrimidin-2-ylbenzenesulfonamide; or 4-[4-chloro-2-(2-piperazin-1-ylpyrimidin-4-yl)phenoxy]-2,5-difluoro-N-pyrimidin-2-ylbenzenesulfonamide;

or a pharmaceutically acceptable salt thereof.

Hereinafter, all references to compounds of the invention include compounds of list (I) or pharmaceutically acceptable salts, solvates, or multi-component complexes thereof, or pharmaceutically acceptable solvates or multi-component complexes of pharmaceutically acceptable salts of compounds of list (I), as discussed in more detail below.

Preferred compounds of the invention are compounds of list (I) or pharmaceutically acceptable salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

The skilled person will appreciate that the aforementioned salts include ones wherein the counterion is optically active, for example d-lactate or l-lysine, or racemic, for example dl-tartrate or dl-arginine.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of list (I) may be prepared by one or more of three methods:

(i) by reacting the compound of list (I) with the desired acid or base;

(ii) by removing an acid- or base-labile protecting group from a suitable precursor of the compound of list (I) using the desired acid or base; or (iii) by converting one salt of the compound of list (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of list (I) or pharmaceutically acceptable salts thereof may exist in both unsolvated and solvated forms. The term 'solvate' is used herein to describe a molecular complex comprising a compound of list (I) or a pharmaceutically acceptable salt thereof and one or more pharmaceutically acceptable solvent molecules, for example, ethanol. The term 'hydrate' is employed when said solvent is water. Pharmaceutically acceptable solvates in accordance with the invention include those wherein the solvent of crystallization may be isotopically substituted, e.g. $D_2O$, $d_6$-acetone and $d_6$-DMSO.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

Also included within the scope of the invention are multi-component complexes (other than salts and solvates) of compounds of list (I) or pharmaceutically acceptable salts thereof wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970), incorporated herein by reference.

The compounds of the invention may be administered as prodrugs. Thus certain derivatives of compounds of list (I) which may have little or no pharmacological activity themselves can, when administered into or onto the body, be converted into compounds of list (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in a compound of list (I) with certain moieties known to those skilled in the art as 'pro-moieties' as described, for example, in "Design of Prodrugs" by H Bundgaard (Elsevier, 1985).

Examples of prodrugs include phosphate prodrugs, such as dihydrogen or dialkyl (e.g. di-tert-butyl)phosphate prodrugs. Further examples of replacement groups in accordance with the foregoing examples and examples of other prodrug types may be found in the aforementioned references.

Also included within the scope of the invention are metabolites of compounds of list (I), that is, compounds formed in vivo upon administration of the drug. Some examples of metabolites in accordance with the invention include, where the compound of list (I) contains a phenyl (Ph) moiety, a phenol derivative thereof (-Ph>-PhOH);

The scope of the invention includes all crystal forms of the compounds of the invention, including racemates and racemic mixtures (conglomerates) thereof. Stereoisomeric conglomerates may also be separated by the conventional techniques described herein just above.

The scope of the invention includes all pharmaceutically acceptable isotopically-labelled compounds of the invention wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of the invention, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of list (I) can generally be prepared by conventional techniques known to those skilled in the art or by processes analogous to those described in the accompanying Examples and Preparations using an appropriate isotopically-labeled reagent in place of the non-labeled reagent previously employed.

Also within the scope of the invention are intermediate compounds as hereinafter defined, all salts, solvates and complexes thereof and all solvates and complexes of salts thereof as defined hereinbefore for compounds of list (I). The invention includes all polymorphs of the aforementioned species and crystal habits thereof.

Compounds of the invention intended for pharmaceutical use may be administered as crystalline or amorphous products or may exist in a continuum of solid states ranging from fully amorphous to fully crystalline. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

In another aspect the invention provides a pharmaceutical composition comprising a compound of the invention together with one or more pharmaceutically acceptable excipients.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

Suitable modes of administration include oral, parenteral, topical, inhaled/intranasal, rectal/intravaginal, and ocular/aural administration.

Formulations suitable for the aforementioned modes of administration may be formulated to be immediate and/or modified release. Modified release formulations include delayed-, sustained-, pulsed-, controlled-, targeted and programmed release.

The compounds of the invention may be administered orally. Oral administration may involve swallowing, so that the compound enters the gastrointestinal tract, or buccal or sublingual administration may be employed by which the compound enters the blood stream directly from the mouth. Formulations suitable for oral administration include solid formulations such as tablets, capsules containing particulates, liquids, or powders, lozenges (including liquid-filled), chews, multi- and nano-particulates, gels, solid solution, liposome, films, ovules, sprays, liquid formulations and buccal/mucoadhesive patches.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet. Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant. Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated. The formulation of tablets is discussed in "Pharmaceutical Dosage Forms: Tablets", Vol. 1, by H. Lieberman and L. Lachman (Marcel Dekker, New York, 1980).

Suitable modified release formulations for the purposes of the invention are described in U.S. Pat. No. 6,106,864. Details of other suitable release technologies such as high energy dispersions and osmotic and coated particles are to be found in "Pharmaceutical Technology On-line", 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of list (I) used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic) acid (PGLA) microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions.

Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™ Bioject™, etc.) injection.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as I-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of list (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

In the case of dry powder inhalers and aerosols, the dosage unit is determined by means of a valve which delivers a metered amount. Units in accordance with the invention are typically arranged to administer a metered dose or "puff" containing from 1 μg to 100 mg of the compound of list (I). The overall daily dose will typically be in the range 1 μg to 200 mg which may be administered in a single dose or, more usually, as divided doses throughout the day.

The compounds of the invention may be administered rectally or vaginally, for example, in the form of a suppository, pessary, microbicide, vaginal ring or enema. Cocoa butter is a traditional suppository base, but various alternatives may be used as appropriate.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 1 mg to 10 g, such as 10 mg to 1 g, for example 25 mg to 500 mg depending, of course, on the mode of administration and efficacy. For example, oral administration may require a total daily dose of from 50 mg to 100 mg. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

As noted above, the compounds of the invention are useful because they exhibit pharmacological activity in animals, i.e., Nav1.7 channel inhibition. More particularly, the compounds of the invention are of use in the treatment of disorders for which a Nav1.7 inhibitor is indicated. Preferably the animal is a mammal, more preferably a human.

In a further aspect of the invention there is provided a compound of the invention for use as a medicament.

In a further aspect of the invention there is provided a compound of the invention for the treatment of a disorder for which a Nav1.7 inhibitor is indicated.

In a further aspect of the invention there is provided use of a compound of the invention for the preparation of a medicament for the treatment of a disorder for which a Nav1.7 inhibitor is indicated.

In a further aspect of the invention there is provided a method of treating a disorder in an animal (preferably a mammal, more preferably a human) for which a Nav1.7 inhibitor is indicated, comprising administering to said animal a therapeutically effective amount of a compound of the invention.

Disorders for which a Nav1.7 inhibitor is indicated include pain, particularly neuropathic, nociceptive and inflammatory pain.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a hightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;

heart and vascular pain, including pain caused by angina, myocardical infarction, mitral stenosis, pericarditis, Raynaud's phenomenon, scleredoma and skeletal muscle ischemia;

head pain, such as migraine (including migraine with aura and migraine without aura), cluster headache, tension-type headache mixed headache and headache associated with vascular disorders;

erythermalgia; and orofacial pain, including dental pain, optic pain, burning mouth syndrome and temporomandibular myofascial pain.

A Nav1.7 inhibitor may be usefully combined with another pharmacologically active compound, or with two or more other pharmacologically active compounds, particularly in the treatment of pain. Such combinations offer the possibility of significant advantages, including patient compliance, ease of dosing and synergistic activity.

In the combinations that follow the compound of the invention may be administered simultaneously, sequentially or separately in combination with the other therapeutic agent or agents.

A Nav1.7 inhibitor of list (I), or a pharmaceutically acceptable salt thereof, as defined above, may be administered in combination with one or more agents selected from:

an alternative Nav1.7 channel modulator, such as another compound of the present invention or a compound disclosed in WO 2009/012242;

an alternative sodium channel modulator, such as a Nav1.3 modulator (e.g. as disclosed in WO2008/118758); or a Nav1.8 modulator (e.g. as disclosed in WO 2008/135826, more particularly N-[6-Amino-5-(2-chloro-5-methoxyphenyl)pyridin-2-yl]-1-methyl-1H-pyrazole-5-carboxamide);

an inhibitor of nerve growth factor signaling, such as: an agent that binds to NGF and inhibits NGF biological activity and/or downstream pathway(s) mediated by NGF signaling (e.g. tanezumab), a TrkA antagonist or a p75 antagonist;

a compound which increases the levels of endocannabinoid, such as a compound with fatty acid amid hydrolase inhibitory (FAAH) activity, in particular those disclosed in WO 2008/047229 (e.g. N-pyridazin-3-yl-4-(3-{[5-(trifluoromethyl)pyridine-2-yl]oxy}benzylidene)piperidene-1-carboxamide);

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetan, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a 5-HT$_3$ antagonist, such as ondansetron a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-Nyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buproprion, buproprion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E$_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl]benzoic acid;

a microsomal prostaglandin E synthase type 1 (mPGES-1) inhibitor;

a leukotriene B4 antagonist, such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870; and a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504).

There is also included within the scope the present invention combinations of a compound of the invention together with one or more additional therapeutic agents which slow down the rate of metabolism of the compound of the invention, thereby leading to increased exposure in patients. Increasing the exposure in such a manner is known as boosting. This has the benefit of increasing the efficacy of the compound of the invention or reducing the dose required to achieve the same efficacy as an unboosted dose. The metabolism of the compounds of the invention includes oxidative processes carried out by P450 (CYP450) enzymes, particularly CYP 3A4 and conjugation by UDP glucuronosyl transferase and sulphating enzymes. Thus, among the agents that may be used to increase the exposure of a patient to a compound of the present invention are those that can act as inhibitors of at least one isoform of the cytochrome P450 (CYP450) enzymes. The isoforms of CYP450 that may be beneficially inhibited include, but are not limited to, CYP1A2, CYP2D6, CYP2C9, CYP2C19 and CYP3A4. Suitable agents that may be used to inhibit CYP 3A4 include ritonavir, saquinavir, ketoconazole, N-(3,4-difluorobenzyl)-N-methyl-2-{[(4-methoxypyridin-3-yl)amino]sulfonyl}benzamide and N-(1-(2-(5-(4-fluorobenzyl)-3-(pyridin-4-yl)-1H-pyrazol-1-yl)acetyl)piperidin-4-yl)methanesulfonamide.

It is within the scope of the invention that two or more pharmaceutical compositions, at least one of which contains a compound of the invention, may conveniently be combined in the form of a kit suitable for coadministration of the compositions. Thus the kit of the invention comprises two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like. The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

In another aspect the invention provides a pharmaceutical product (such as in the form of a kit) comprising a compound of the invention together with one or more additional therapeutically active agents as a combined preparation for simultaneous, separate or sequential use in the treatment of a disorder for which a Nav1.7 inhibitor is indicated.

It is to be appreciated that all references herein to treatment include curative, palliative and prophylactic treatment.

The compounds of the invention may be prepared by any method known in the art for the preparation of compounds of analogous structure. In particular, the compounds of the invention can be prepared by the specific methods described in the Examples, or by similar processes thereto.

The skilled person will appreciate that the experimental conditions set forth in the Examples that follow illustrate suitable conditions for effecting the transformations, that it may be desirable to vary the precise conditions employed, and further that it may be desirable to carry out the transformations in a different order from that described.

In addition, the skilled person will appreciate that it may be desirable at any stage in the synthesis of compounds of the invention to protect one or more sensitive groups, so as to prevent undesirable side reactions. In particular, it may be desirable to protect amino groups. The protecting groups used in the preparation of the compounds of the invention may be used in conventional manner. See, for example, those described in 'Greene's Protective Groups in Organic Synthesis' by Theodora W Greene and Peter G M Wuts, fourth edition, (John Wiley and Sons, 2006), in particular chapter 7 ("Protection for the Amino Group"), incorporated herein by reference, which also describes methods for the removal of such groups.

When preparing a compound of the invention, a person skilled in the art may select the form of intermediate which provides the best combination of features for this purpose. Such features include the melting point, solubility, processability and yield of the intermediate form and the resulting ease with which the product may be purified on isolation.

Conventional techniques for the preparation/isolation of individual enantiomer precursors include chiral synthesis from a suitable optically pure precursor or resolution of the racemate (or the racemate of a salt or derivative) using, for example, chiral high pressure liquid chromatography (HPLC).

Alternatively, a racemic precursor may be reacted with a suitable optically active compound, for example, an alcohol, or, in the case where the compound contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral precursors may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Mixtures of stereoisomers may be separated by conventional techniques known to those skilled in the art; see, for example, "Stereochemistry of Organic Compounds" by E. L. Eliel and S. H. Wilen (Wiley, New York, 1994.

The invention is illustrated by the following non-limiting examples in which the following abbreviations and definitions may be used:

DMSO means dimethyl sulphoxide;

GCMS means gas chromatography mass spectroscopy;

HPLC means high performance liquid chromnatography;

LCMS means liquid chromatography mass spectroscopy;

NaOH means sodium hydroxide; and $NH_4Cl$ means ammonium chloride.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents: $CDCl_3$, deuterochloroform; $d_6$-DMSO, deuterodimethylsulphoxide.

Mass spectra (m/z) were recorded using either electrospray ionisation (ESI) or atmospheric pressure chemical ionisation (APCI). When relevant, and unless stated otherwise, the m/z data provided are for isotopes $^{19}$F, $^{35}$Cl and $^{79}$Br.

Where compounds were purified by HPLC and/or analysed by LCMS the following methods were used:

Preparative Reverse Phase HPLC Methods:

a) Phenomenex 250×30 mm 15 micron C18 column. 40 mL/minutes. Gradient 85% A to 100% B over 25 minutes. Solvent A: 7800 water/200 acetonitrile/8 trifluoroacetic acid. Solvent B: 7200 acetonitrile/800 water/8 trifluoroacetic acid, 254 nM UV detection.

b) Phenomenex 100×21.2 mm 10 micron C18 column. 20 mL/minutes. Gradient 85% A to 100% B over 25 minutes. Solvent A: 7800 water/200 acetonitrile/8 trifluoroacetic acid. Solvent B: 7200 acetonitrile/800 water/8 trifluoroacetic acid, 254 nM UV detection.

LC/MS Analysis

Mass spectrometry data was acquired on a Sciex API150 with MassChrom software interfaced to a Michrom Magic HPLC and CTC autosampler. MS scan data were obtained by alternately scanning positive and negative ion from 40 to 800 daltons with a 0.1 dalton step and a 0.15 msec dwell time. The ionization voltage was 4000 for positive ion (−4200 for negative ion) with the temperature at 400 C, nebulizer gas set to 7, and the curtain gas set to 8. Lens and ring voltages were periodically optimized. HPLC flow rate was 500 µL/min during the 1 minute gradient from 20% buffer B to 98% buffer B on a 1×25 mm 5 micron 100A C18AQ Magic Bullet from Michrom Bioresources. The flow rate was increased to 700 µL/min with the gradient held at 98% B for 1.2 minutes. The composition of buffer A was water with 0.1% formic acid and buffer B was methanol with 1% water and 0.1% formic acid.

EXAMPLE 1

5-Chloro-4-[4-chloro-2-(2-piperazin-1-ylpyrimidin-4-yl)phenoxy]-2-fluoro-N-1,3-thiazol-4-ylbenzenesulfonamide trifluoroacetate

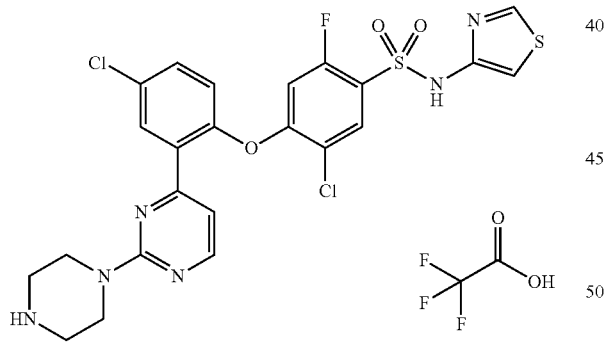

tert-Butyl 4-[4-(5-chloro-2-hydroxyphenyl)pyrimidin-2-yl]piperazine-1-carboxylate (Preparation 2, 48.6 mg, 0.11 mmol), tert-butyl[(5-chloro-2,4-difluorophenyl)sulfonyl]1,3-thiazol-4-ylcarbamate (Preparation 4, 43.6 mg, 0.11 mmol) and potassium carbonate (21.9 mg, 0.16 mmol) were mixed in dimethylsulfoxide (1 mL) and shaken at ambient temperature for 18 hours. The reaction mixture was diluted with water and the precipitate collected by filtration. The solid was dissolved in dichloromethane (2.0 mL) and dried over anhydrous magnesium sulfate. The mixture was filtered and trifluoroacetic acid (0.060 mL, 0.78 mmol) was added to the filtrate. After 2 hours the reaction mixture was concentrated in vacuo to a residue and purified by reverse phase HPLC to afford the title compound as a tan glass (55 mg).

$^1$HNMR (d$_6$-DMSO): δ 3.12 (m, 4H), 3.83 (m, 4H), 7.04-7.12 (m, 3H), 7.32 (d, 1H), 7.65 (dd, 1H), 7.93-7.96 (m, 2H), 8.48 (d, 1H), 8.76 (br s, 2H), 8.92 (d, 1H).

LCMS Rt=1.63 min MS m/z 581 [MH]+

EXAMPLE 2

5-Chloro-4-[4-chloro-2-(2-piperazin-1-ylpyrimidin-4-yl)phenoxy]-2-fluoro-N-1,3,4-thiadiazol-2-ylbenzenesulfonamide trifluoroacetate

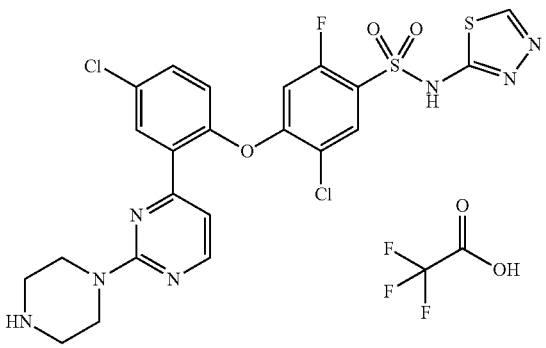 [SMILES: O=S(=O)(Nc1nncs1)c1cc(Cl)c(Oc2ccc(Cl)cc2-c2ccnc(N3CCNCC3)n2)cc1F ; O=C(O)C(F)(F)F]

tert-Butyl 4-[4-(5-chloro-2-hydroxyphenyl)pyrimidin-2-yl]piperazine-1-carboxylate (Preparation 2, 48.6 mg, 0.11 mmol), 5-chloro-N-(2,4-dimethoxybenzyl)-2,4-difluoro-N-(1,3,4-thiadiazol-2-yl)benzenesulfonamide (Preparation 6, 49.1 mg, 0.11 mmol) and potassium carbonate (21.9 mg, 0.16 mmol) were mixed in dimethylsulfoxide (1 mL) and shaken at ambient temperature for 18 hours. The reaction mixture was diluted with water and the precipitate collected by filtration. The solid was dissolved in dichloromethane (2.0 mL) and dried over anhydrous magnesium sulfate. The mixture was filtered and trifluoroacetic acid (0.060 mL, 0.78 mmol) was added to the filtrate. After 2 hours the reaction mixture was concentrated in vacuo to a residue and purified by reverse phase HPLC to afford the title compound as a tan glass (35.5 mg).

$^1$HNMR (d$_6$-DMSO): δ 3.13 (br s, 4H), 3.84 (br s, 4H), 7.06-7.12 (m, 2H), 7.31 (d, 1H), 7.64 (dd, 1H), 7.92 (d, 1H), 7.96 (d, 1H), 8.49 (d, 1H), 8.76 (br s, 2H), 8.83 (s, 1H).

LCMS Rt=1.59 min MS m/z 582 [MH]+

EXAMPLE 3

5-Chloro-2-fluoro-4-[5-fluoro-2-pyridazin-4-yl-4-(trifluoromethyl)phenoxy]-N-1,3-thiazol-4-ylbenzenesulfonamide

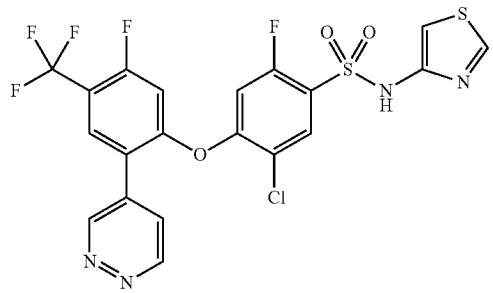 [SMILES: O=S(=O)(Nc1cscn1)c1cc(Cl)c(Oc2cc(F)c(C(F)(F)F)cc2-c2ccnnc2)cc1F]

A mixture of 5-fluoro-2-pyridazin-4-yl-4-(trifluoromethyl)phenol (Preparation 9, 2.81 g, 10.9 mmol), tert-butyl [(5-chloro-2,4-difluorophenyl)sulfonyl]1,3-thiazol-4-ylcarbamate (Preparation 4, 5.59 g, 13.6 mmol) and potassium carbonate (4.51 g, 32.6 mmol) in dimethylsulfoxide (20 mL) was heated at 75° C. for 24 hours. The reaction mixture was cooled to ambient temperature, diluted with water, neutralized with saturated aqueous ammonium chloride, then extracted with ethyl acetate (×3). The combined organic layers were washed with brine, dried over anhydrous sodium sulfate, filtered, and concentrated in vacuo. The residue was purified via automated silica gel flash chromatography using two runs, (10% to 100% ethyl acetate in hexanes gradient elution for run 1, and 0% to 10% methanol in dichloromethane gradient elution for run 2) to afford the title compound as a brown solid. (2.42 g, 41%)

$^1$HNMR (d$_6$-DMSO): δ 7.15 (d, 1H), 7.50-7.72 (m, 2H), 7.90-8.06 (m, 2H), 8.20 (d, 1H), 8.95 (d, 1H), 9.35 (d, 1H), 9.51 (s, 1H), 11.53 (br s, 1H).

LCMS Rt=1.69 min MS m/z 549 [MH]+

EXAMPLE 3A

5-Chloro-2-fluoro-4-[5-fluoro-2-pyridazin-4-yl-4-(trifluoromethyl)phenoxy]-N-1,3-thiazol-4-ylbenzenesulfonamide 4-methylbenzenesulfonate

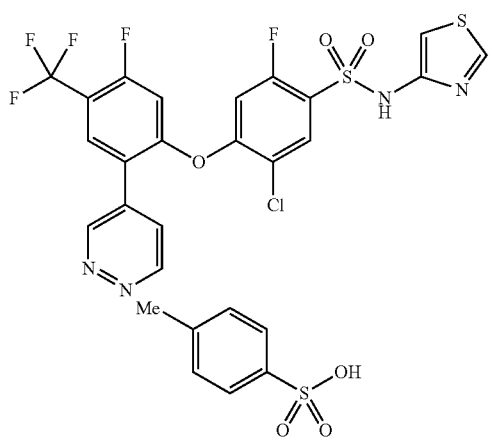

A solution of p-toluenesulfonic acid monohydrate (0.851 g, 4.41 mmol) in acetone (10 mL) was added to a solution of 5-chloro-2-fluoro-4-[5-fluoro-2-pyridazin-4-yl-4-(trifluoromethyl)phenoxy]-N-1,3-thiazol-4-ylbenzenesulfonamide (2.42 g, 4.41 mmol) in acetone (15 mL). After stirring at ambient temperature for 15 minutes, the reaction mixture was concentrated in vacuo. The residue was suspended in diethyl ether (75 mL) and stirred for 2 hours. The resulting solid was collected by filtration, dried, and then recrystallized from ethyl acetate-heptane-methanol (20:10:1) to afford the title compound as a tan crystalline solid (1.78 g, 56%).

$^1$HNMR (d$_6$-DMSO): δ 2.31 (s, 3H), 7.08-7.21 (m, 3H), 7.45-7.71 (m, 4H), 7.95-8.10 (m, 2H), 8.22 (d, 1H), 8.95 (d, 1H), 9.38 (d, 1H), 9.54 (s, 1H), 11.53 (br s, 1H).

LCMS Rt=1.67 min MS m/z 549 [MH]+

EXAMPLE 4

5-Chloro-2-fluoro-4-[4-fluoro-2-pyridazin-4-yl-5-(trifluoromethyl)phenoxy]-N-1,3-thiazol-4-ylbenzenesulfonamide bis(trifluoroacetate)

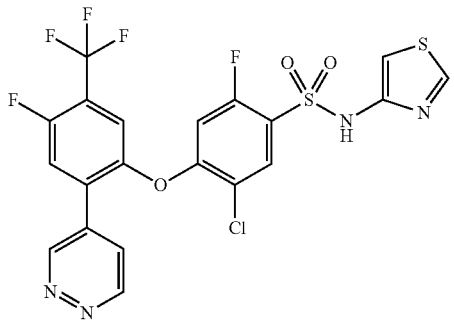

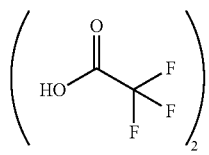

A 1.0 M solution of lithium hexamethyldisilazide in tetrahydrofuran (7.55 mL, 7.55 mmol) was added to a solution of 4-fluoro-2-pyridazin-4-yl-5-(trifluoromethyl)phenol (Preparation 11, 1.30 g, 5.04 mmol) in N,N-dimethylformamide (30 mL). After stirring for 5 minutes, tert-butyl-[(5-chloro-2,4-difluorophenyl)sulfonyl]1,3-thiazol-4-ylcarbamate (Preparation 4, 2.07 g, 5.04 mmol) was added and the reaction mixture stirred at ambient temperature. After 18 hours, the reaction mixture was diluted with water, neutralized with saturated aqueous ammonium chloride, and extracted with ethyl acetate (×3). The combined organic layers were washed with brine, dried over anhydrous sodium sulfate, filtered, and concentrated onto diatomaceous earth. The residue was purified by automated silica gel flash chromatography (hexanes to ethyl acetate gradient elution) to afford tert-butyl({5-chloro-2-fluoro-4-[4-fluoro-2-pyridazin-4-yl-5-(trifluoromethyl)phenoxy]phenyl}sulfonyl)1,3-thiazol-4-ylcarbamate (1.75 g).

LCMS Rt=1.76 min MS m/z 649 [MH]+

Trifluoroacetic acid (9 mL) was added to a solution of tert-butyl({5-chloro-2-fluoro-4-[4-fluoro-2-pyridazin-4-yl-5-(trifluoromethyl)phenoxy]phenyl}sulfonyl)1,3-thiazol-4-ylcarbamate (2.0 g, 3.1 mmol) in dichloromethane (20 mL). After 2 hours, the reaction mixture was concentrated in vacuo to afford the title compound as an amber foam (2.37 g).

$^1$HNMR (d$_6$-DMSO): δ 7.07 (d, 1H), 7.20 (d, 1H), 7.83-7.92 (m, 3H), 8.07 (d, 1H), 8.89 (d, 1H), 9.33 (m, 1H), 9.40 (m, 1H).

LCMS Rt=1.67 min MS m/z 549 [MH]+

EXAMPLE 4A

5-Chloro-2-fluoro-4-[4-fluoro-2-pyridazin-4-yl-5-(trifluoromethyl)phenoxy]-N-1,3-thiazol-4-ylbenzenesulfonamide 4-methylbenzenesulfonate

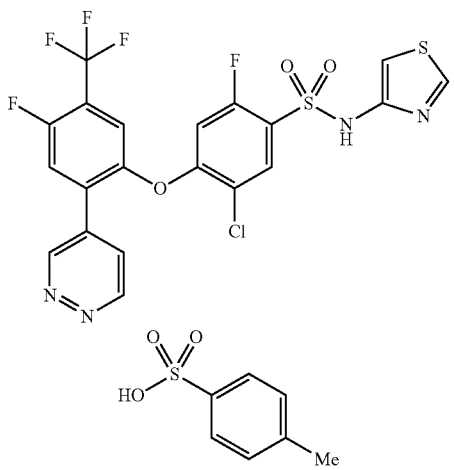

A solution of 1.0 M potassium hydroxide in water (65 mL, 65 mmol) was added to 5-chloro-2-fluoro-4-[4-fluoro-2-pyridazin-4-yl-5-(trifluoromethyl)phenoxy]-N-1,3-thiazol-4-ylbenzenesulfonamide bis(trifluoroacetate) (2.37 g, 3.05 mmol). The mixture was stirred at ambient temperature. Diethyl ether was added and the layers separated. The aqueous layer was acidified to pH 4 with 10 wt % citric acid in water. A precipitate developed so the mixture was sonicated then stirred for 45 minutes at ambient temperature. The aqueous layer was extracted with ethyl acetate (4×50 mL). The combined organic layers were washed with brine, dried over anhydrous sodium sulfate, treated with charcoal, filtered through diatomaceous earth, and concentrated in vacuo. The residue was taken up in acetone and ether and concentrated in vacuo to give 5-chloro-2-fluoro-4-[4-fluoro-2-pyridazin-4-yl-5-(trifluoromethyl)phenoxy]-N-1,3-thiazol-4-ylbenzenesulfonamide as a solid which was used without further purification.

A solution of 4-methylbenzenesulfonic acid (0.489 g, 2.84 mmol) in acetone (6 mL) was added to a solution of 5-chloro-2-fluoro-4-[4-fluoro-2-pyridazin-4-yl-5-(trifluoromethyl)phenoxy]-N-1,3-thiazol-4-ylbenzenesulfonamide (1.56 g, 2.84 mmol) in acetone. The solution was stirred for 15 min, filtered, and concentrated in vacuo to give title compound as a tan foam which was used without further purification.

Seed crystals of the title compound were generated by dissolving a small portion (~50 mg) of the crude title compound as a tan foam in a minimal amount of hot 2-butanone. Heptane was added to the solution until slightly cloudy. The mixture was warmed to produce a clear solution, and the side of the vial was scratched with a glass pipette to promote the formation of crystals. The resulting crystals were collected by filtration and set aside for use as seed crystals in a batch-wise crystallization.

The remainder of the title compound as a tan foam was dissolved in a minimal amount of hot 2-butanone. The solution was stirred while adding heptane in a dropwise manner. Upon remaining slightly cloudy, the solution was warmed slightly to produce a clear solution. Seed crystals of the title compound were added while stirring; solid formed rapidly in the mixture. The solids were diluted with ice cold 2:1 heptane:2-butanone, collected by filtration, and washed with additional cold 2:1 heptane:2-butanone. The sample was dried in vacuo to afford the title compound as a white powder (1.73 g, 79%).

$^1$HNMR (d$_6$-DMSO): δ 2.29 (br s, 3H), 7.07 (d, 1H), 7.11 (m, 2H), 7.21 (d, 1H), 7.47 (m, 2H), 7.83-7.92 (m, 3H), 8.07 (d, 1H), 8.89 (d, 1H), 9.33 (m, 1H), 9.41 (m, 1H).

LCMS Rt=1.67 min MS m/z 549 [MH]+

EXAMPLE 5

4-[2-(2-Aminopyridin-4-yl)-4-chlorophenoxy]-5-chloro-2-fluoro-N-(5-fluoropyrimidin-2-yl)benzenesulfonamide dihydrochloride

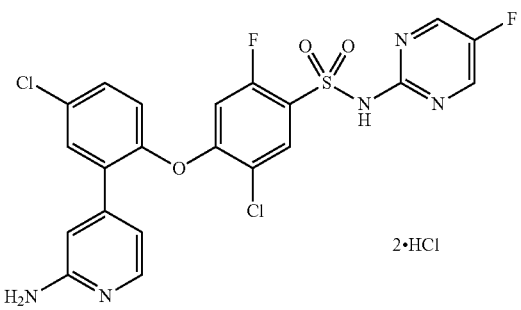 [SMILES: Nc1cc(-c2cc(Cl)ccc2Oc2cc(F)c(S(=O)(=O)Nc3ncc(F)cn3)cc2Cl)ccn1]

To a solution of 4-[2-(2-aminopyridin-4-yl)-4-chlorophenoxy]-5-chloro-N-(ethoxymethyl)-2-fluoro-N-(5-fluoropyrimidin-2-yl)benzenesulfonamide (Preparation 15, 67 mg, 0.12 mmol) in methanol (1 mL) was added a 2.0 M solution of hydrogen chloride in water (1 mL, 2.00 mmol). The reaction mixture was heated at 60° C. for 6 hours then concentrated in vacuo. The residue was freeze dried from acetonitrile-water to afford the title compound as a white solid (69 mg).

$^1$HNMR (d$_6$-DMSO): δ 6.95 (m, 1H), 7.05 (m, 1H), 7.22 (d, 1H), 7.20 (d, 1H), 7.63 (m, 1H), 7.73 (m, 1H), 7.95-8.06 (m, 4H), 8.65 (s, 2H).

LCMS Rt=1.35 min MS m/z 524 [MH]+

EXAMPLE 6

4-[2-(2-Aminopyridin-4-yl)-4-(trifluoromethyl)phenoxy]-5-chloro-2-fluoro-N-(5-fluoropyrimidin-2-yl)benzenesulfonamide 4-methylbenzenesulfonate

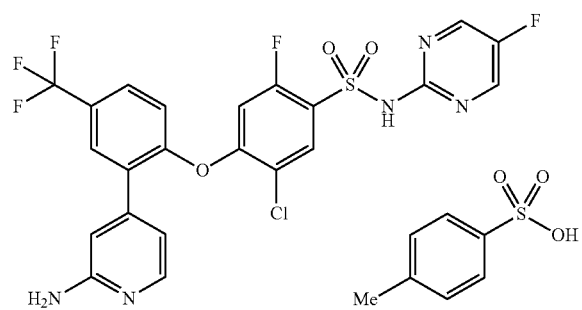 [SMILES: Nc1cc(-c2cc(C(F)(F)F)ccc2Oc2cc(F)c(S(=O)(=O)Nc3ncc(F)cn3)cc2Cl)ccn1 ; Cc1ccc(S(=O)(=O)O)cc1]

4-[2-(2-Aminopyridin-4-yl)-4-(trifluoromethyl)phenoxy]-5-chloro-N-(2,4-dimethoxybenzyl)-2-fluoro-N-(5-fluoropyrimidin-2-yl)benzenesulfonamide (Preparation 20, 2.24 g, 3.16 mmol) was dissolved in 1,4-dioxane (6.0 mL) and a 4.0 M solution of hydrogen chloride in 1,4-dioxane (4.0 mL, 16 mmol) was added. The reaction mixture was stirred for 18 hours then concentrated in vacuo. The residue was partitioned between water and dichloromethane. A large amount of undissolved solid was present. The aqueous phase was adjusted to pH10 with 1N aqueous sodium hydroxide solution, then back to pH3 with citric acid. The mixture was filtered and the solid was set aside. The organic phase was collected and combined with the solid and the solvent removed in vacuo. The residue was purified by silica gel column chromatography (0 to 10% methanol in dichloromethane gradient elution). The resulting residue was then slurried in methanol before 1 equivalent of 4-methylbenzenesulfonic acid was added and the mixture concentrated in vacuo. The residue was dissolved in a minimum amount of hot methanol and filtered while hot. The filtrate was diluted with tert-butyl methyl ether. Crystals formed on standing which were collected by filtration and washed with tert-butyl methyl ether to afford the title compound as a white solid (1.48 g containing 0.5 mol % tert-butyl methyl ether). The solid was dissolved in a minimum amount of boiling methanol, then water was added slowly. Fine crystals formed which were collected by filtration and rinsed with water to afford the title compound as a white powder (1.45 g).

$^1$HNMR (d$_6$-DMSO): δ 2.28 (s, 3H), 7.03 (d, 1H), 7.06-7.14 (m, 3H), 7.34 (d, 1H), 7.47 (d, 2H), 7.75-8.02 (m, 5H), 8.11 (d, 1H), 8.66 (s, 1H). 3 exchangeables not observed LCMS Rt=1.41 min MS m/z 558 [MH]+

EXAMPLE 7

4-[2-(2-Aminopyridin-4-yl)-4-fluorophenoxy]-5-chloro-2-fluoro-N-1,3-thiazol-4-ylbenzenesulfonamide trifluoroacetate

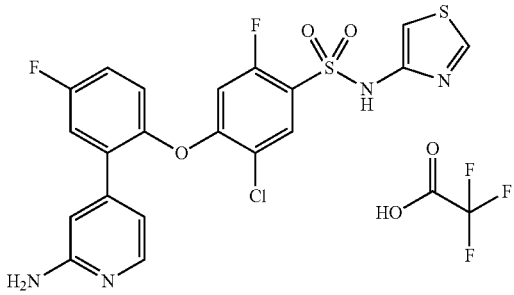 [SMILES: Nc1cc(-c2cc(F)ccc2Oc2cc(F)c(S(=O)(=O)Nc3cscn3)cc2Cl)ccn1 ; O=C(O)C(F)(F)F]

tert-Butyl[(5-chloro-2,4-difluorophenyl)sulfonyl]1,3-thiazol-4-ylcarbamate (Preparation 4, 60 mg, 0.15 mmol) was added to a mixture of 2-(2-aminopyridin-4-yl)-4-fluorophenol (Preparation 21, 30 mg, 0.1 mmol) and potassium carbonate (41 mg, 0.29 mmol) in dimethylsulfoxide (2 mL) and stirred at ambient temperature for 24 hours. The reaction mixture was poured into saturated aqueous ammonium chloride and water and extracted with ethyl acetate. The combined organic layers were washed with brine, dried over anhydrous sodium sulfate, filtered, and concentrated in vacuo. The residue was taken up in dichloromethane, concentrated onto diatomaceous earth, and purified by automated silica gel flash chromatography (100% hexanes to 20% methanol in ethyl acetate, gradient elution) to afford tert-butyl({4-[2-(2-aminopyridin-4-yl)-4-fluorophenoxy]-5-chloro-2-fluorophenyl}sulfonyl)1,3-thiazol-4-ylcarbamate as a light brown oil, which was used without further purification.

LCMS Rt=1.43 minutes, MS m/z 495 [M(-Boc)H]+

A 4.0 M solution of hydrogen chloride in 1,4-dioxane (1.5 mL, 5.9 mmol) was added to a solution of the intermediate in methanol (2.3 mL) and heated at 65° C. for 3 hours. The reaction mixture was concentrated in vacuo. The residue was purified by preparative HPLC to afford the title compound as a white powder (43.5 mg).

$^1$HNMR (d$_6$-DMSO): δ 6.97 (d, 1H), 7.03-7.21 (m, 3H), 7.34-7.57 (m, 2H), 7.61 (dd, 1H), 7.89-8.04 (m, 2H), 8.11 (br s, 2H), 8.94 (d, 1H), 11.46 (br s, 1H).

LCMS Rt=1.25 min MS m/z 495 [MH]+

EXAMPLE 8

4-[2-(3-Amino-1H-pyrazol-4-yl)-4-(trifluoromethoxy)phenoxy]-5-chloro-2-fluoro-N-1,3-thiazol-4-ylbenzenesulfonamide dihydrochloride

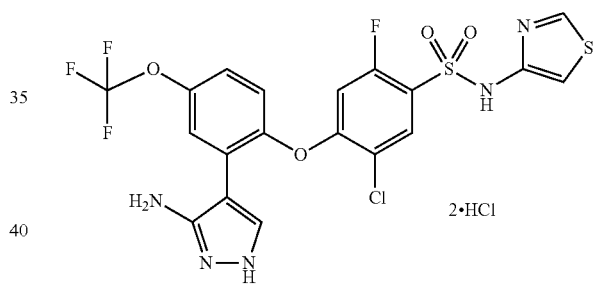

tert-Butyl[(5-chloro-2-fluoro-4-{2-[3-nitro-1-(tetrahydro-2H-pyran-2-yl)-1H-pyrazol-4-yl]-4-(trifluoromethoxy)phenoxy}phenyl)sulfonyl]1,3-thiazol-4-ylcarbamate (Preparation 25, 3.70 g, 4.84 mmol), and saturated aqueous ammonium chloride solution (17 mL) were added to ethanol (62 mL). A white precipitate formed. Iron (0.541 g, 9.68 mmol) was added and the reaction mixture heated at 80° C. After 2 hours the reaction mixture was cooled, filtered and concentrated in vacuo. The residue was slurried in water and the solid collected by filtration. The solid was rinsed with water, then dissolved in ethyl acetate, dried over anhydrous magnesium sulfate and concentrated in vacuo. The residue was dissolved in a saturated solution of hydrogen chloride in methanol and heated at 50° C. for 2 hours. The solvent was removed in vacuo and the residue dissolved in a minimum amount of methanol. Ethyl acetate was added and the solution stirred for 4 hours while crystals formed. The solid was collected by filtration to afford the title compound as a white powder (1.75 g).

$^1$HNMR (d$_6$-DMSO): δ 7.03 (d, 1H), 7.11 (d, 1H), 7.28 (d, 1H), 7.41 (m, 1H), 7.65 (d, 1H), 7.92 (d, 1H), 7.95 (s, 1H), 8.92 (d, 1H), 11.44 (s, 1H)

LCMS Rt=1.63 min MS m/z 550 [MH]+

EXAMPLE 9

4-[2-(2-Aminopyridin-4-yl)-4-chlorophenoxy]-3-chloro-N-1,3,4-thiadiazol-2-ylbenzenesulfonamide trifluoroacetate

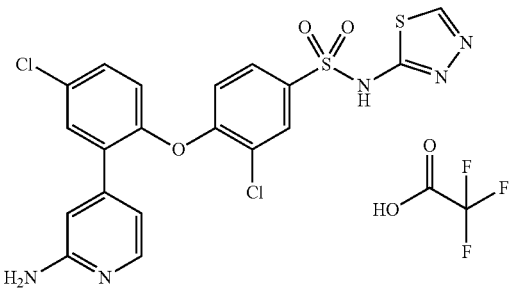 [SMILES: Nc1cc(-c2cc(Cl)ccc2Oc2ccc(S(=O)(=O)Nc3nncs3)cc2Cl)ccn1 ; O=C(O)C(F)(F)F]

3-Chloro-N-(2,4-dimethoxybenzyl)-4-fluoro-N-1,3,4-thiadiazol-2-ylbenzenesulfonamide (Preparation 26, 106 mg, 0.24 mmol) and 2-(2-aminopyridin-4-yl)-4-chlorophenol (Preparation 13, 52.5 mg, 0.24 mmol) were dissolved in N,N-dimethylformamide (0.62 mL) and potassium carbonate (49.3 mg, 0.36 mmol) was added. The reaction mixture was heated at 65° C. for 4 hours. The reaction mixture was cooled to ambient temperature, diluted with water, and extracted with ethyl acetate. The combined organic phase was dried over anhydrous magnesium sulfate, filtered, and then concentrated in vacuo to afford the dimethoxybenzyl intermediate as a light brown oil, which was used without further purification.

LCMS Rt=1.59 min MS m/z 644 [MH]+

Trifluoroacetic acid (0.183 mL, 2.38 mmol) was added to a solution of the dimethoxybenzyl intermediate in dichloromethane (1.8 mL) and stirred at ambient temperature for 1 hour. The reaction mixture was concentrated in vacuo and the residue purified by preparative HPLC to afford the title compound as a white powder (59 mg).

$^1$HNMR (d$_6$-DMSO): δ 7.01 (d, 1H), 7.10 (s, 1H), 7.16-7.30 (m, 2H), 7.65 (dd, 1H), 7.70-7.83 (m, 2H), 7.87-8.14 (m, 4H), 8.33 (s, 1H). 1 exchangeable not observed LCMS Rt=1.55 min MS m/z 494 [MH]+

EXAMPLE 10

4-[2-(2-Aminopyridin-4-yl)-4-chlorophenoxy]-5-chloro-2-fluoro-N-1,3-thiazol-4-ylbenzenesulfonamide trifluoroacetate

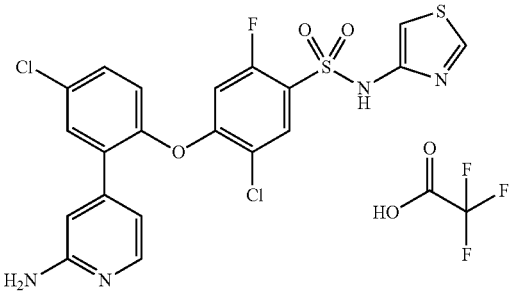 [SMILES: Nc1cc(-c2cc(Cl)ccc2Oc2cc(F)c(S(=O)(=O)Nc3cscn3)cc2Cl)ccn1 ; O=C(O)C(F)(F)F]

tert-Butyl[(5-chloro-2,4-difluorophenyl)sulfonyl]1,3-thiazol-4-ylcarbamate (Preparation 4, 61.8 mg, 0.15 mmol) was added to a mixture of 2-(2-aminopyridin-4-yl)-4-chlorophenol (Preparation 13, 33.2 mg, 0.15 mmol) and potassium carbonate (41.6 mg, 0.30 mmol) in dimethylsulfoxide (2 mL). The reaction mixture was stirred at ambient temperature. After 24 hours, the reaction mixture was poured into saturated aqueous ammonium chloride and water, and extracted with ethyl acetate. The combined organic layers were washed with brine, dried over anhydrous sodium sulfate, filtered, and concentrated in vacuo to afford the carbamate intermediate as a light brown oil, which was used without further purification.

LCMS Rt=1.47 min MS m/z 611 [MH]+

A solution of 4.0 M hydrogen chloride in 1,4-dioxane (1.5 mL) was added to a solution of the carbamate intermediate in methanol (2.0 mL) and heated at 65° C. for 3 hours. The reaction mixture was concentrated in vacuo and the residue purified by preparative HPLC to afford the title compound as a white powder (58 mg).

$^1$HNMR (d$_6$-DMSO): δ 7.00 (d, 1H), 7.08 (s, 1H), 7.14 (d, 1H), 7.22-7.39 (m, 2H), 7.68 (d, 1H), 7.76 (dd, 1H), 7.91-8.20 (m, 4H), 8.95 (d, 1H), 11.50 (br s, 1H).

LCMS Rt=1.43 min MS m/z 511 [MH]+

EXAMPLE 11

4-[2-(5-Amino-1H-pyrazol-4-yl)-4-fluorophenoxy]-5-chloro-2-fluoro-N-1,3-thiazol-4-ylbenzenesulfonamide trifluoroacetate

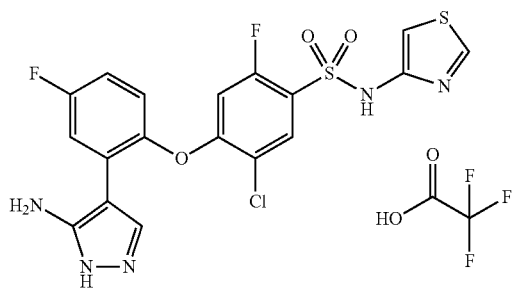 [SMILES: Nc1[nH]ncc1-c1cc(F)ccc1Oc1cc(F)c(S(=O)(=O)Nc2cscn2)cc1Cl ; O=C(O)C(F)(F)F]

To a solution of tert-butyl[(5-chloro-2-fluoro-4-{4-fluoro-2-[3-nitro-1-(tetrahydro-2H-pyran-2-yl)-1H-pyrazol-4-yl]phenoxy}phenyl)sulfonyl]1,3-thiazol-4-ylcarbamate (Preparation 28, 85 mg, 0.12 mmol) in ethanol (3 mL) was added saturated aqueous ammonium chloride solution (0.4 mL) and iron (68 mg, 1.2 mmol). The reaction mixture was heated at 80° C. for 4 hours then cooled to ambient temperature. Sodium sulfate (2 g) was added and the mixture was stirred for 15 minutes, then filtered through diatomaceous earth and washed with 10% methanol in ethyl acetate. The filtrate was concentrated in vacuo to afford the carbamate intermediate as a pale yellow solid, which was used without purification.

LCMS Rt=1.76 min MS m/z 568 [M(-Boc)H]$^+$

A solution of 4.0 M hydrogen chloride in 1,4-dioxane (1 mL, 5 mmol) was added to a solution of the carbamate intermediate in methanol (2.0 mL) and heated at 50° C. for 2 hours. The reaction mixture was concentrated in vacuo and the residue purified by preparative HPLC to afford the title compound as a white powder (47 mg).

$^1$HNMR (d$_6$-DMSO): δ 6.74 (d, 1H), 7.12 (s, 1H), 7.17-7.40 (m, 2H), 7.50 (dd, 1H), 7.71 (s, 1H), 7.93 (d, 1H), 8.95 (s, 1H), 11.43 (br s, 1H).

LCMS Rt=1.59 min MS m/z 484 [MH]+

EXAMPLE 12

5-Chloro-2-fluoro-4-[2-pyridazin-4-yl-4-(trifluoromethoxy)phenoxy]-N-1,3-thiazol-4-ylbenzenesulfonamide trifluoroacetate

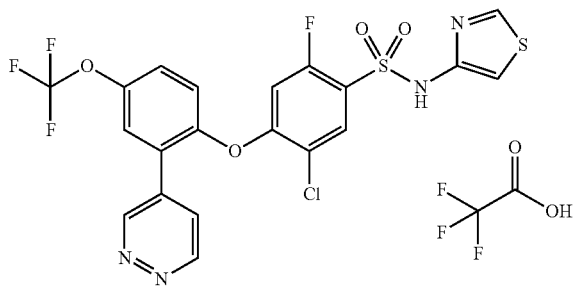 [SMILES: O=S(=O)(Nc1cscn1)c1cc(Cl)c(Oc2ccc(OC(F)(F)F)cc2-c2ccnnc2)cc1F ; O=C(O)C(F)(F)F]

2-Pyridazin-4-yl-4-(trifluoromethoxy)phenol (Preparation 30, 88 mg, 0.34 mmol) was dissolved in dimethylsulfoxide (4 mL). Potassium carbonate (90 mg, 0.65 mmol) was added, followed by tert-butyl[(5-chloro-2,4-difluorophenyl)sulfonyl]1,3-thiazol-4-ylcarbamate (Preparation 4, 141 mg, 0.34 mmol). The reaction mixture was stirred for 18 hours at ambient temperature then diluted with water and extracted with ethyl ether (×3). The combined organic phase was concentrated in vacuo and purified by silica gel column chromatography (hexanes to ethyl acetate gradient elution). The residue was dissolved in saturated hydrogen chloride in methanol and stirred for 18 hours at ambient temperature. The reaction mixture was concentrated in vacuo and purified by reverse phase HPLC to afford the title compound as an off-white powder (133 mg).

$^1$HNMR (d$_6$-DMSO): δ 7.10 (d, 1H), 7.30 (d, 1H), 7.36 (d, 1H), 7.56 (m, 1H), 7.85 (d, 1H), 7.88 (dd, 1H), 7.93 (d, 1H), 8.91 (d, 1H), 9.30 (dd, 1H), 9.44 (dd, 1H).

LCMS Rt=1.66 min MS m/z 547 [MH]+

EXAMPLE 13

4-[2-(1-Azetidin-3-yl-1H-pyrazol-5-yl)-5-chloro-2-fluoro-4-(trifluoromethyl)phenoxy]-N-1,3,4-thiadiazol-5-ylbenzenesulfonamide

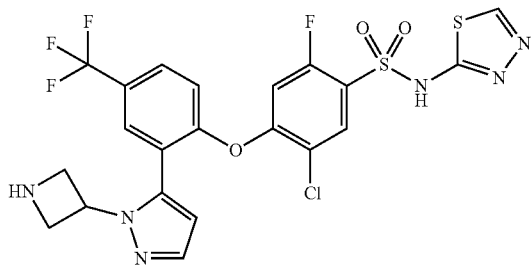 [SMILES: O=S(=O)(Nc1nncs1)c1cc(Cl)c(Oc2ccc(C(F)(F)F)cc2-c2ccnn2C2CNC2)cc1F]

tert-Butyl 3-{5-[5-trifluoromethyl-2-(2-chloro-4-{[(2,4-dimethoxybenzyl)(1,3,4-thiadiazol-5-yl)amino]sulfonyl}-5-fluorophenoxy)phenyl]-1H-pyrazol-1-yl}azetidine-1-carboxylate (Preparation 35, 590 mg, 0.72 mmol) was dissolved in dichloromethane (10 mL). Trifluoroacetic acid (2 mL) was added dropwise and the solution stirred at ambient temperature for 2.5 hours. The reaction mixture was concentrated in vacuo and the residue slurried in methanol (20 mL) before concentrating in vacuo again. This was repeated twice more. Finally the residue was again slurried in methanol (20 mL) and the solid removed by filtration. The filtrate was concentrated in vacuo to give a foam. Water (50 mL) was added followed by 0.880 aqueous ammonia (5 mL) to give a white solid which was collected by filtration, washed with methanol and dried in vacuo to afford the title compound as a white solid (360 mg, 88%).

$^1$HNMR (d$_6$-DMSO): δ 4.26 (m, 4H), 5.23 (m, 1H), 4.53 (s, 1H), 7.16 (d, 1H), 7.33 (m, 1H), 7.82 (m, 4H), 8.57 (s, 1H), 8.83 (br s, 1H).

LCMS Rt=1.23 mins MS m/z 575 [M$^{35}$ClH]+

EXAMPLE 14

5-Chloro-2-fluoro-4-{4-trifluoromethyl-2-[1-(1-methylazetidin-3-yl)-1H-pyrazol-5-yl]phenoxy}-N-1,3,4-thiadiazol-ylbenzenesulfonamide

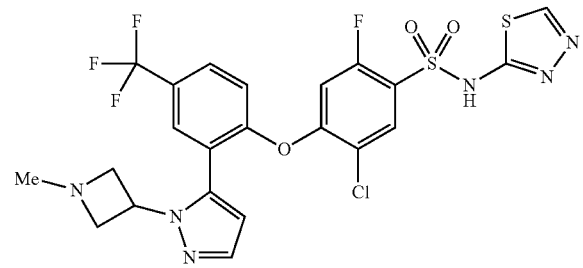 [SMILES: CN1CC(n2nccc2-c2cc(C(F)(F)F)ccc2Oc2cc(F)c(S(=O)(=O)Nc3nncs3)cc2Cl)C1]

4-[2-(1-Azetidin-3-yl-1H-pyrazol-5-yl)-5-chloro-2-fluoro-4-(trifluoromethyl)phenoxy]-N-1,3,4-thiadiazol-5-ylbenzenesulfonamide (Example 13, 100 mg, 0.17 mmol) was stirred in dichloromethane (5 mL), methanol (0.5 mL) and acetic acid (0.015 mL) at 0° C. Aqueous formaldehyde (0.04 mL of 37% wt/vol) was added and the reaction mixture stirred at 0° C. for 15 minutes. Sodium triacetoxyborohydride (120 mg, 0.56 mmol) was added and the mixture stirred for 3 hours. The reaction mixture was concentrated in vacuo and the residue dissolved in ethyl acetate and extracted with saturated aqueous sodium hydrogen carbonate solution (2×10 mL) and brine (2×10 mL). The organic layer was separated, dried over sodium sulphate, filtered and evaporated to give a solid. The compound was purified by silica gel flash column chromatography (90:10 dichloromethane:methanol to 80:10:10 dichloromethane:methanol:acetic acid gradient elution) to give a gum. The gum was suspended in water and basified with 0.880 aqueous ammonia. The resulting solid was collected by filtration and dried to afford the title compound as a white solid (25 mg, 24%).

$^1$HNMR (d$_6$-DMSO): δ 2.84 (s, 3H), 4.17 (m, 2H), 4.30 (m, 2H) 5.19 (s, 1H), 6.52 (d, 1H), 7.17 (d, 1H) 7.32 (m, 1H), 7.80 (m, 4H), 8.58 (s, 1H)

LCMS Rt=18 min MS m/z 589 [M$^{35}$ClH]+

EXAMPLE 15

3-Cyano-4-[2-(3-methylpyridazin-4-yl)-4-(trifluoromethyl)phenoxy]-N-1,2,4-thiadiazol-5-ylbenzenesulfonamide

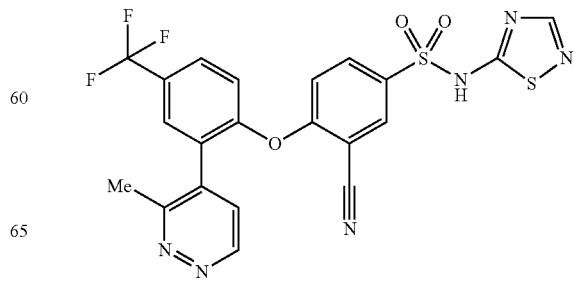

2-(3-Methylpyridazin-4-yl)-4-(trifluoromethyl)phenol (Preparation 44, 100 mg, 0.38 mmol) and 3-cyano-4-fluoro-N-(1,2,4-thiadiazol-5-yl)benzenesulfonamide (Preparation 39, 108 mg, 0.38 mmol) were dissolved in dimethylsulfoxide (2 mL). Potassium carbonate (157 mg, 1.14 mmol) was added and the reaction mixture was heated to 90° C. for 4 hours. The reaction mixture was cooled and the crude material purified by reverse phase column chromatography (ISCO™ Companion, C18 silica, 5% to 60% acetonitrile in water gradient elution) to afford the title compound as an off-white solid (130 mg).

¹HNMR (d₆-DMSO): δ 2.51 (s, 3H), 7.12 (d, 1H), 7.49 (d, 1H), 7.59 (d, 1H), 7.91 (m, 5H), 9.06 (d, 1H).

LCMS Rt=1.62 min MS m/z 519 [MH]+

EXAMPLE 16

3-Methyl-4-[2-pyridazin-4-yl-4-(trifluoromethyl) phenoxy]-N-1,2,4-thiadiazol-5-ylbenzenesulfonamide

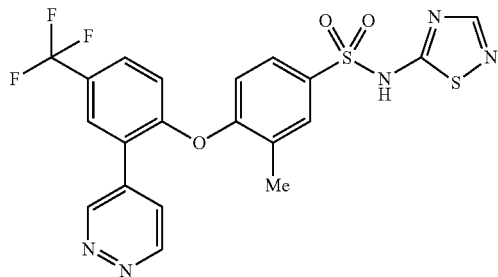 [SMILES: Cc1cc(S(=O)(=O)Nc2ncns2)ccc1Oc1ccc(C(F)(F)F)cc1-c1ccnnc1]

A Reactivial™ containing trimethylboroxine (798 mg, 6.36 mmol), 1,1-bis(diphenylphosphino)ferrocenepalladium (II)dichloride, complex with dichloromethane (26 mg, 0.03 mmol), potassium carbonate (88 mg, 0.64 mmol), N-(2,4-dimethoxybenzyl)-3-iodo-4-[2-pyridazin-4-yl-4-(trifluoromethyl)phenoxy]-N-1,2,4-thiadiazol-5-ylbenzenesulfonamide (Preparation 38, 240 mg, 0.32 mmol) and 2-methyltetrahydrofuran (5 mL) was sparged with nitrogen and heated to 80° C. for 24 hours. The reaction mixture was cooled and purified directly by silica gel column chromatography (0% to 20% methanol in ethyl acetate gradient elution) followed by reverse phase HPLC to afford the title compound.

¹HNMR (CD₃OD): δ 2.28 (s, 3H), 7.05 (d, 1H), 7.10 (d, 1H), 7.70 (d, 1H), 7.80 (m, 2H), 8.00 (m, 2H), 8.20 (s, 1H), 9.20 (d, 1H), 9.50 (s, 1H).

LCMS Rt=3.40 minutes. MS m/z 987 [2MH]+

EXAMPLE 17

4-[4-chloro-2-(2-piperazin-1-ylpyrimidin-4-yl)phenoxy]2,5-difluoro-N-1,3-thiazol-4-ylbenzenesulfonamide trifluoroacetate

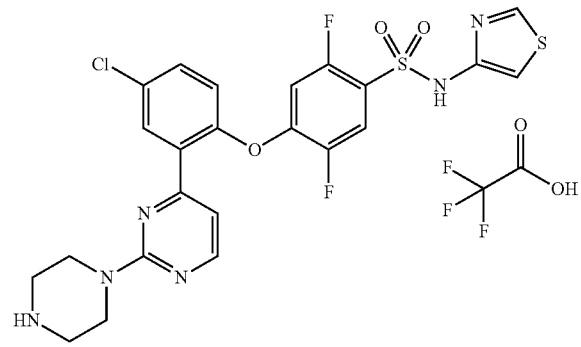

tert-Butyl 4-[4-(5-chloro-2-hydroxyphenyl)pyrimidin-2-yl]piperazine-1-carboxylate (Preparation 2, 48.6 mg, 0.11 mmol), tert-butyl 1,3-thiazol-4-yl[(2,4,5-trifluorophenyl) sulfonyl]carbamate (Preparation 45, 41.9 mg, 0.11 mmol) and potassium carbonate (21.9 mg, 0.16 mmol) were mixed in dimethylsulfoxide (1 mL) and shaken at ambient temperature for 18 hours. The reaction was diluted with water and the precipitate collected by filtration. The solid was dissolved in dichloromethane (2 mL), and dried over anhydrous magnesium sulfate. The mixture was filtered and trifluoroacetic acid (0.06 mL, 0.78 mmol) was added to the filtrate. After 2 hours the reaction was concentrated in-vacuo and purified by reverse phase HPLC to afford the title compound as a tan glass (52 mg).

¹HNMR (d₆-DMSO/D₂O): δ 3.16 (m, 4H), 3.89 (m, 4H), 7.12 (m, 2H), 7.20 (dd, 1H), 7.37 (d, 1H), 7.67 (dd, 1H), 7.84 (dd, 1H), 7.97 (d, 1H), 8.51 (d, 1H), 8.95 (d, 1H).

LCMS Rt=1.59 min MS m/z 565 [MH]+

Examples 18-21 have also been prepared.

EXAMPLES 18

4-[4-chloro-2-(2-piperazin-1-ylpyridin-4-yl)phenoxy]-2,5-difluoro-N-pyrimidin-2-ylbenzenesulfonamide

EXAMPLE 19

4-[4-chloro-2-(2-piperazin-1-ylpyridin-4-yl)phenoxy]-3-cyano-N-pyrimidin-2-ylbenzenesulfonamide

EXAMPLE 20

4-[4-chloro-2-(2-piperazin-1-ylpyrimidin-4-yl)phenoxy]-3-cyano-N-pyrimidin-2-ylbenzenesulfonamide

EXAMPLE 21

4-[4-chloro-2-(2-piperazin-1-ylpyrimidin-4-yl)phenoxy]-2,5-difluoro-N-pyrimidin-2-ylbenzenesulfonamide

Preparation 1

4-Chloro-2-(2-chloropyrimidin-4-yl)phenol

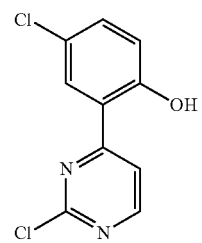 [SMILES: Oc1ccc(Cl)cc1-c1ccnc(Cl)n1]

A mixture of 2,4-dichloropyrimidine (0.765 g, 5.03 mmol), (5-chloro-2-hydroxyphenyl)boronic acid (0.568 g, 3.30 mmol), 2.0 M aqueous sodium carbonate (2.82 mL, 5.64 mmol), and 1,2-dimethoxyethane (8 mL) was sparged for 10 minutes with argon. Tetrakis(triphenylphosphine)palladium (0) (0.217 g, 0.19 mmol) was added, and the resultant mixture was heated for 4 hours at 85° C. The reaction mixture mixture was cooled to 0° C., quenched with saturated aqueous ammonium chloride solution, and extracted with dichloromethane (×3). The combined organic layers were washed with brine, dried over anhydrous sodium sulfate, filtered, and concentrated in vacuo. The residue was purified by automated silica gel flash chromatography (hexanes to ethyl acetate gradient elution) to afford the title compound as a yellow solid (61.5 mg, 7%).

¹HNMR (d₆-DMSO): δ 7.06 (d, 1H), 7.45 (m, 1H), 8.00 (d, 1H), 8.28 (d, 1H), 8.81 (d, 1H), 11.21 (s, 1H).
LCMS Rt=1.74 min MS m/z 241 [MH]+

Preparation 2 tert-Butyl 4-[4-(5-chloro-2-hydroxyphenyl)pyrimidin-2-yl]piperazine-1-carboxylate

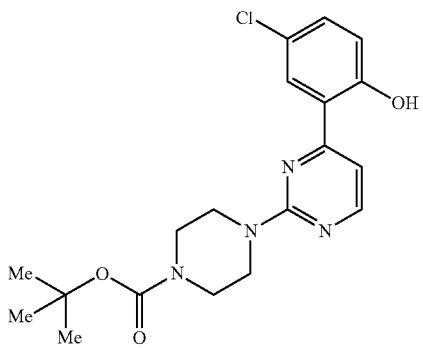 [SMILES: CC(C)(C)OC(=O)N1CCN(c2nccc(-c3cc(Cl)ccc3O)n2)CC1]

tert-Butyl piperazine-1-carboxylate (24.0 mg, 0.13 mmol) was added to a mixture of 4-chloro-2-(2-chloropyrimidin-4-yl)phenol (Preparation 1, 30.1 mg, 0.13 mmol), and triethylamine (61.2 uL, 0.44 mmol) in isopropyl alcohol (0.2 mL). The reaction mixture was stirred at ambient temperature. After 18 hours, LCMS analysis indicated the reaction was not complete. The reaction mixture was heated for 30 minutes at 70° C. then cooled to ambient temperature. The reaction mixture was diluted with ethyl acetate, washed with water then brine, dried over anhydrous sodium sulfate, filtered, and concentrated in vacuo to afford the title compound as a light brown paste (50 mg).
¹HNMR (d₆-DMSO): δ 1.43 (s, 9H), 3.47 (m, 4H), 3.73 (m, 4H), 6.98 (d, 1H), 7.40 (m, 1H), 7.46 (d, 1H), 8.03 (d, 1H), 8.52 (d, 1H).
LCMS Rt=2.02 min MS m/z 391 [MH]+

Preparation 3

Thiazole-4-yl-carbamic acid tert-butyl ester

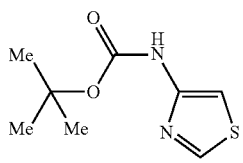 [SMILES: CC(C)(C)OC(=O)Nc1cscn1]

Thiazole-4-carboxylic acid (6.46 g, 50.0 mmol) was slurried in tert-butyl alcohol (280 mL). Triethylamine (7.68 mL, 55.1 mmol) and diphenylphosphonic azide (11.9 mL, 55.1 mmol) were added and the reaction mixture heated at reflux for 18 hours. The reaction mixture was concentrated in vacuo and the residue dissolved in ethyl acetate. The organics were washed successively with water, 5% aqueous citric acid solution, water, saturated aqueous sodium bicarbonate and brine. The organic phase was dried over anhydrous magnesium sulfate and concentrated in vacuo. The residue was purified by silica gel chromatography (ISCO™ column, hexanes to ethyl acetate gradient elution) then triturated with 20% tert-butylmethyl ether in hexanes. The solid was collected by filtration and dried in vacuo to afford the title compound as a white solid (6.48 g).
¹HNMR (CDCl₃): δ 1.46 (s, 9H), 7.23 (m, 1H), 8.89 (d, 1H).
LCMS Rt=1.46 min MS m/z 201 [MH]+

Preparation 4 tert-Butyl[(5-chloro-2,4-difluorophenyl)sulfonyl]1,3-thiazol-4-ylcarbamate

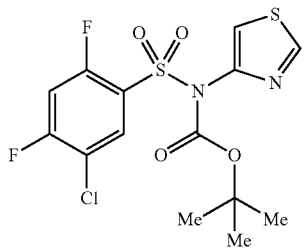 [SMILES: CC(C)(C)OC(=O)N(c1cscn1)S(=O)(=O)c1cc(Cl)c(F)cc1F]

To a solution of thiazol-4-yl-carbamic acid tert-butyl ester (Preparation 3, 503 mg, 2.51 mmol) in tetrahydrofuran (5.0 mL) cooled to −78° C. was added lithium hexamethyldisilazide (1.0 M in tetrahydrofuran, 2.76 mL, 2.76 mmol). The reaction mixture was stirred for 30 minutes at ambient temperature then cooled to −78° C. A solution of 5-chloro-2,4-difluorobenzenesulfonyl chloride (620.5 mg, 2.51 mmol) in tetrahydrofuran (5.0 mL) was added slowly via a syringe. After the addition was complete, the reaction mixture was allowed to warm gradually to ambient temperature. After 24 hours, the reaction mixture was poured into saturated aqueous ammonium chloride solution and extracted with ethyl acetate. The combined organic extracts were dried over anhydrous magnesium sulfate, filtered and concentrated in vacuo onto diatomaceous earth. The residue was purified by automated silica gel flash chromatography (0% to 5% ethyl acetate in dichloromethane gradient elution) to afford the title compound as a white solid (733 mg).
¹HNMR (d₆-DMSO): δ 1.40 (s, 9H), 7.10 (m, 1H), 7.52 (m, 1H), 8.25 (t, 1H), 8.80 (m, 1H).
LCMS Rt=1.70 min MS m/z 311 [M(-Boc)H]⁺

Preparation 5

N-(2,4-Dimethoxybenzyl)-1,3,4-thiadiazol-2-amine

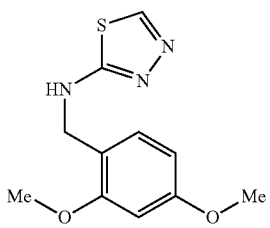 [SMILES: COc1ccc(CNc2nncs2)c(OC)c1]

To a solution of 2-amino-1,3,4-thiadiazole (3.05 g, 30.2 mmol) and 2,4-dimethoxy-benzaldehyde (4.55 g, 27.4 mmol) in dichloromethane (125 mL) was added chlorotriisopropoxytitanium (16 mL, 67 mmol) portionwise over 5 minutes.

After stirring for 1 hour, sodium triacetoxyborohydride (11.72 g, 55.3 mmol) was added portion wise and stirred for 24 hours. The reaction was quenched with saturated aqueous sodium bicarbonate solution, adjusted to pH 9 with sodium hydroxide (6 N aqueous solution) and extracted with dichloromethane. The combined organic extracts were dried over anhydrous magnesium sulfate, filtered and concentrated in vacuo. The residue was purified by silica gel flash column chromatography (0% to 10% methanol in dichloromethane gradient elution) to afford the title compound as a white solid (590 mg).

$^1$HNMR (CDCl$_3$): δ 3.86 (s, 3H), 3.90 (s, 3H), 4.49 (m, 2H), 6.08 (br s, 1H), 6.47 (m, 2H), 7.27 (m, 1H), 8.39 (s, 1H).

LCMS Rt=1.36 min MS m/z 252 [MNa]+

Preparation 6

5-Chloro-N-(2,4-dimethoxybenzyl)-2,4-difluoro-N-1,3,4-thiadiazol-2-ylbenzenesulfonamide

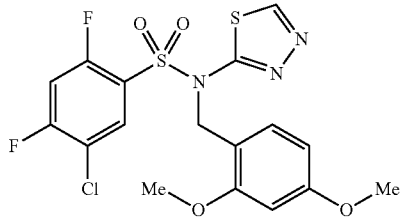 [SMILES: COc1ccc(CN(c2nncs2)S(=O)(=O)c2cc(Cl)c(F)cc2F)c(OC)c1]

To a solution of N-(2,4-dimethoxybenzyl)-1,3,4-thiadiazol-2-amine (Preparation 5, 899 mg, 3.58 mmol) in tetrahydrofuran (6.0 mL) cooled to −78° C., was added lithium hexamethyldisilazide (1.0 M in tetrahydrofuran, 4.3 mL) dropwise. The reaction mixture was stirred for 35 minutes at ambient temperature, then cooled again to −78° C. before the dropwise addition of 5-chloro-2,4-difluorobenzenesulfonyl chloride (850 mg, 3.4 mmol). The reaction mixture was stirred at −78° C. for 1 hour then at ambient temperature for 4 hours. The reaction mixture was poured into saturated aqueous ammonium chloride solution and extracted with dichloromethane. The combined organic layers were washed with saturated aqueous sodium chloride solution, dried over anhydrous magnesium sulfate, filtered and concentrated in vacuo. The residue was purified by automated silica gel flash chromatography (0% to 10% ethyl acetate in hexanes gradient elution) to afford the title compound as a white solid (1.16 g, 73%).

$^1$HNMR (CDCl$_3$): δ 3.71 (s, 3H), 3.78 (s, 3H), 5.35 (m, 2H), 6.26 (m, 1H), 6.38 (m, 1H), 6.99 (m, 1H), 7.27 (m, 1H), 7.83 (m, 1H), 8.87 (m, 1H).

LCMS Rt=1.76 min MS m/z 484 [MNa]+

Preparation 7

3-Fluoro-4-(trifluoromethyl)phenol

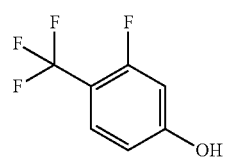

A solution of OXONE® (1.50 g, 2.45 mmol) in water (7.8 mL) was added drop-wise over approximately 4 minutes to a solution of 2-[3-fluoro-4-(trifluoromethyl)phenyl]-4,4,5,5-tetramethyl-1,3,2-dioxaborolane (710 mg, 2.4 mmol) in acetone (7.8 mL). A precipitate formed during addition of the OXONE®. The reaction mixture was stirred vigorously for 15 minutes then quenched with 10% w/v aqueous solution of sodium metabisulfite (20 mL). The aqueous layer was extracted with dichloromethane (×3), dried over anhydrous sodium sulfate, filtered, and concentrated in vacuo to afford the title compound as a light yellow oil which was used without purification in the next step.

LCMS Rt=1.65 min MS m/z 179 [MH]−

Preparation 8

5-Fluoro-2-iodo-4-(trifluoromethyl)phenol

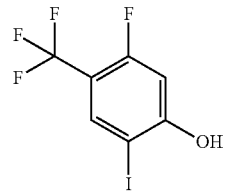

A solution of iodine (0.874 g, 3.44 mmol) in chloroform (17.1 mL) was added in a drop-wise manner over 1.5 hours to a mixture of 3-fluoro-4-(trifluoromethyl)phenol (Preparation 7, 620 mg, 3.4 mmol) and silver trifluoroacetate (0.760 g, 3.44 mmol) in chloroform (3.4 mL). On completion of the addition, the reaction mixture was stirred for 1 hour. The reaction mixture was then filtered through diatomaceous earth, and the filtrate washed successively with 10% w/v aqueous sodium thiosulfate, half-saturated aqueous sodium bicarbonate, water and brine. The organic phase was dried over anhydrous sodium sulfate, filtered, and concentrated onto diatomaceous earth. The residue was purified by automated silica gel flash chromatography (100% hexanes to 50% dichloromethane in hexanes gradient elution) and concentrated in vacuo to afford the title compound as a light yellow oil (579 mg).

$^1$HNMR (d$_6$-DMSO): δ 6.85 (d, 1H), 7.97 (d, 1H), 11.81 (s, 1H).

LCMS Rt=1.79 min MS m/z 305 [MH]−

Preparation 9

5-Fluoro-2-pyridazin-4-yl-4-(trifluoromethyl)phenol

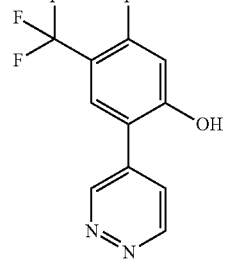

Cesium fluoride (570 mg, 3.8 mmol), tetrakis(triphenylphosphine)palladium(0) (220 mg, 0.19 mmol), and copper(I) iodide (72 mg, 0.38 mmol) were added to a solution of 5-fluoro-2-iodo-4-(trifluoromethyl)phenol (Preparation 8, 579 mg, 1.89 mmol) and 4-(tributylstannyl)pyridazine (770 mg, 2.1 mmol) in N,N-dimethylformamide (4 mL). The reaction mixture was heated at 45° C. under an atmosphere of argon. After 1.5 hours, the reaction mixture was cooled to ambient temperature, diluted with ethyl acetate and water, and filtered through diatomaceous earth. The layers were separated, and the organic layer was washed with water, aqueous lithium chloride, and brine. The organic layer was dried over anhydrous sodium sulfate, filtered, and concentrated in vacuo. The residue was taken up in dichloromethane, concentrated onto diatomaceous earth, and purified by automated silica gel flash chromatography (100% dichloromethane to 10% methanol in dichloromethane gradient elution) to afford the title compound as a tan solid (305 mg).

$^1$HNMR (d$_6$-DMSO): δ 6.99 (d, 1H), 7.87 (d, 1H), 7.93 (m, 1H), 9.26 (m, 1H), 9.49 (m, 1H), 11.74 (s, 1H).

LCMS Rt=1.57 min MS m/z 259 [MH]+

Preparation 10

4-Fluoro-2-iodo-5-(trifluoromethyl)phenol

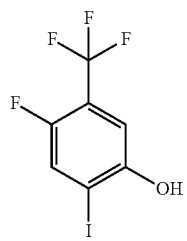

Concentrated sulfuric acid (0.78 mL. 15.0 mmol) was added to a mixture of 4-fluoro-3-(trifluoromethyl)phenol (8.00 g, 44.4 mmol) and N-iodosuccinimide (5.00 g, 22.2 mmol) in acetic acid (40 mL) at 0° C. After 1 hour, the ice bath was removed and an additional portion of N-iodosuccinimide (1.50 g. 6.67 mmol) added. After an additional 1 hour at ambient temperature, the final portion of N-iodosuccinimide (1.0 g, 4.4 mmol) was added. The reaction mixture was stirred for 1 hour then diluted with water (300 mL), treated with 20 wt % aqueous sodium thiosulfate, and extracted with ether (3×100 mL). The combined organic layers were washed with aqueous sodium thiosulfate then brine, dried over anhydrous sodium sulfate, filtered, and concentrated in vacuo. The residue was purified by automated silica gel flash chromatography (100% hexanes to 50% dichloromethane in hexanes gradient elution) to afford the title compound as a yellow oil (8.1 g).

$^1$HNMR (d$_6$-DMSO): δ 7.12 (d, 1H), 7.92 (d, 1H).

LCMS Rt=1.70 min MS m/z 305 [MH]−

Preparation 11

4-Fluoro-2-pyridazin-4-yl-5-(trifluoromethyl)phenol

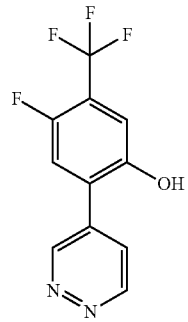 [SMILES: Oc1cc(C(F)(F)F)c(F)cc1-c1ccnnc1]

Cesium fluoride (790 mg, 5.2 mmol), tetrakis(triphenylphosphine)palladium(0) (300 mg, 0.26 mmol), and copper(I) iodide (100 mg, 0.52 mmol) were added to a solution of 4-fluoro-2-iodo-5-(trifluoromethyl)phenol (Preparation 10, 800 mg, 2.6 mmol) and 4-(tributylstannyl)pyridazine (1.1 g, 2.9 mmol) in N,N-dimethylformamide (6 mL). The reaction mixture was heated at 45° C. under an atmosphere of argon. After 1 hour, the reaction mixture was cooled to ambient temperature, diluted with ethyl acetate and water, and filtered through diatomaceous earth. The solids were washed with additional ethyl acetate. The layers were separated, and the organic layer washed with water, aqueous lithium chloride and brine, then dried over anhydrous sodium sulfate, filtered, and concentrated in vacuo. The residue was taken up in dichloromethane, concentrated onto diatomaceous earth, and purified by automated silica gel flash chromatography (100% dichloromethane to 10% methanol in dichloromethane gradient elution) to afford the title compound as an orange solid (598 mg).

$^1$HNMR (d$_6$-DMSO): δ 7.28 (d, 1H), 7.77 (d, 1H), 7.98 (m, 1H), 9.33 (br s, 1H), 9.53 (br s, 1H).

LCMS Rt=1.49 min MS m/z 259 [MH]+

Preparation 12

5-Chloro-2,4-difluoro-N-(5-fluoropyrimidin-2-yl)benzenesulfonamide

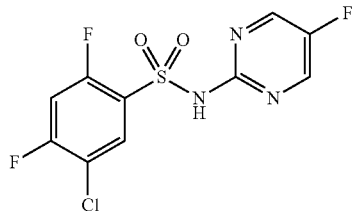 [SMILES: O=S(=O)(Nc1ncc(F)cn1)c1cc(Cl)c(F)cc1F]

A suspension of 5-chloro-2,4-difluorobenzenesulfonyl chloride (1.99 g, 8.05 mmol) in dichloromethane (15 mL) was added portion-wise to a solution of 5-fluoro-pyrimidin-2-ylamine (1.00 g, 8.84 mmol) in pyridine (15 mL) at 0° C. The reaction mixture was then allowed to warm to ambient temperature gradually and stirred for 16 hours. The reaction mixture was diluted with dichloromethane and partitioned with 1 N aqueous hydrogen chloride solution. The layers were separated and the aqueous layer extracted with dichloromethane. The combined organic layers were washed with water, diluted with ethyl acetate, dried over anhydrous sodium sulfate, filtered and concentrated in vacuo. The residue was purified by automated silica gel column chromatography (100% chloroform to 10% methanol in chloroform gradient elution) to afford the title compound as a light yellow solid (0.32 g).

$^1$HNMR (d$_6$-DMSO): δ 7.85 (m, 1H), 8.17 (m, 1H), 8.67 (s, 2H).

LCMS Rt=1.53 min MS m/z 324 [MH]+

Preparation 13

2-(2-Aminopyridin-4-yl)-4-chlorophenol

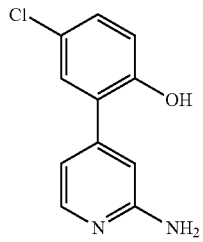 [SMILES: Nc1cc(-c2cc(Cl)ccc2O)ccn1]

A suspension of 2-amino-4-chloropyridine (13 g, 101 mmol), (5-chloro-2-hydroxy)benzeneboronic acid (20.9 g, 121 mmol), tetrakis triphenylphosphine palladium (11.7 g, 10.1 mmol) and sodium carbonate (42.9 g, 404 mmol) in water (120 mL) and 1,4-dioxane (360 mL) was heated to 90° C. under nitrogen for 24 hours. The reaction mixture was cooled, concentrated in vacuo and the residue extracted into ethyl acetate (500 mL) before filtration. The filtrate was washed with 2N aqueous hydrogen chloride solution (500 mL) and water (700 mL). The combined aqueous layer was basified with saturated aqueous sodium bicarbonate solution (1500 mL) before extracting with ethyl acetate (2×800 mL). The organic layer was dried over anhydrous sodium sulfate and concentrated in vacuo. The residue was purified by silica gel column chromatography (2% to 12% methanol in dichloromethane gradient elution) to afford the title compound as a yellow solid (11.13 g).

$^1$HNMR (400 MHz, d$_6$-DMSO): δ 5.80 (br s, 2H), 6.60 (m, 2H), 6.95 (m, 1H), 7.20 (m, 1H), 7.90 (m, 1H), 9.95 (m, 1H).

LCMS Rt=1.58 min MS m/z 221 [MH]+

Preparation 14

5-Chloro-N-(ethoxymethyl)-2,4-difluoro-N-(5-fluoropyrimidin-2-yl)benzenesulfonamide

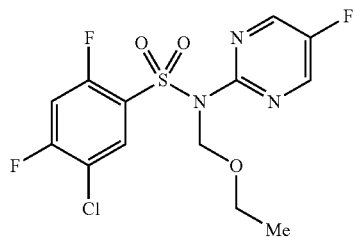 [SMILES: CCOCN(c1ncc(F)cn1)S(=O)(=O)c1cc(Cl)c(F)cc1F]

To a solution of 5-chloro-2,4-difluoro-N-(5-fluoropyrimidin-2-yl)benzenesulfonamide (Preparation 12, 0.28 g, 0.86 mmol) in dichloromethane (7 mL) at 0° C. was added N,N-diisopropylethylamine (0.23 mL, 1.32 mmol) and chloromethyl ethyl ether (0.088 mL, 0.95 mmol). The reaction mixture was stirred for 20 hours allowing the solution to gradually warm to ambient temperature. The reaction mixture was diluted with ethyl acetate, washed with 1N aqueous sodium hydroxide solution, water, and brine and then dried over anhydrous sodium sulphate and concentrated in vacuo. The residue was purified by silica gel column chromatography (hexanes to ethyl acetate gradient elution) to afford the title compound as a white solid (173 mg).

$^1$HNMR (d$_6$-DMSO): δ 1.15 (t, 3H), 3.63 (q, 2H), 5.62 (s, 2H), 7.89 (t, 1H), 8.25 (t, 1H), 8.78 (s, 2H).

LCMS Rt=1.68 min MS m/z 382 [MH]+

Preparation 15

4-[2-(2-Aminopyridin-4-yl)-4-chlorophenoxy]-5-chloro-N-(ethoxymethyl)-2-fluoro-N-(5-fluoropyrimidin-2-yl)benzenesulfonamide

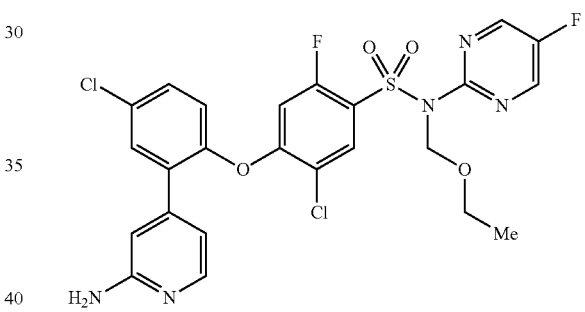

To a solution of 5-chloro-N-(ethoxymethyl)-2,4-difluoro-N-(5-fluoropyrimidin-2-yl)benzenesulfonamide (Preparation 14, 75 mg, 0.20 mmol) in dimethylsulfoxide (1 mL) was added 2-(2-aminopyridin-4-yl)-4-chlorophenol (Preparation 13, 43.3 mg, 0.20 mmol) and potassium carbonate (40.7 mg, 0.30 mmol). The reaction mixture was stirred at 50° C. for 19 hours, then diluted with ethyl acetate (30 mL) and washed with 1N aqueous sodium hydroxide solution, water and brine, dried over anhydrous sodium sulfate, filtered and concentrated in vacuo. The residue was purified by silica gel column chromatography (50% hexanes in ethyl acetate to 100% ethyl acetate gradient elution) to afford the title compound as a white solid (68 mg).

$^1$HNMR (d$_6$-DMSO): δ 1.13 (t, 3H), 3.60 (q, 2H), 5.57 (s, 2H), 6.00 (s, 2H), 6.53 (m, 2H), 6.96 (d, 1H), 7.34 (d, 1H), 7.59 (m, 2H), 7.82 (d, 1H), 8.09 (d, 1H), 8.74 (s, 2H).

LCMS Rt=1.57 min MS m/z 582 [MH]+

Preparation 16

4-[2-Methoxy-5-(trifluoromethyl)phenyl]pyridin-2-amine

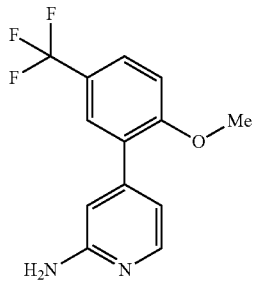

Argon was bubbled through a suspension of 2-methoxy-5-trifluoromethylphenylboronic acid (2.3 g, 10 mmol), 2-amino-4-bromopyridine (2.0 g, 12 mmol), and sodium carbonate (4.4 g, 42 mmol) in 1,4-dioxane (30 mL) and water (9 mL) for 15 minutes, then tetrakis(triphenylphosphine)palladium(0) (1.2 g, 1.0 mmol) was added. The resulting mixture was heated at 85° C. for 18 hours. The reaction mixture was cooled to ambient temperature then diluted with ethyl acetate and water. The phases were separated and the aqueous phase extracted with ethyl acetate then choloroform. The combined organic extracts were dried over anhydrous sodium sulfate and concentrated in vacuo. The residue was purified by silica gel column chromatography (0% to 10% methanol in chloroform gradient elution) to afford the title compound as yellow oil (3.22 g).

$^1$HNMR (d$_6$-DMSO): δ 3.86 (s, 3H), 5.95 (s, 2H), 6.56 (s, 1H), 6.62 (m, 1H), 7.31 (d, 1H), 7.54 (s, 1H), 7.75 (m, 1H), 7.93 (d, 1H).

LCMS Rt=1.16 min MS m/z 269 [MH]+

Preparation 17

2-(2-Aminopyridin-4-yl)-4-(trifluoromethyl)phenol

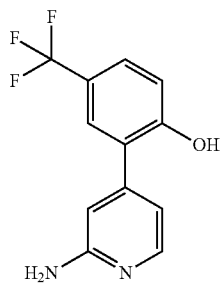 [SMILES: Nc1cc(-c2cc(C(F)(F)F)ccc2O)ccn1]

To 4-[2-methoxy-5-(trifluoromethyl)phenyl]pyridin-2-amine (Preparation 16, 2.8 g, 0.01 mmol) in dichloromethane (5 mL) at 0° C. was added drop-wise a 1.0 M solution of boron tribromide in dichloromethane (31.3 mL, 31.3 mmol). After stirring for 20 hours at ambient temperature, the reaction mixture was quenched with water and saturated aqueous sodium bicarbonate until basic. The aqueous phase was extracted with 15% isopropyl alcohol in chloroform (×3). The combined organic phase was dried over anhydrous sodium sulfate, filtered and concentrated in vacuo. The residue was purified by silica gel column chromatography (0% to 10% methanol in chloroform gradient elution) and concentrated in vacuo to afford the title compound as a yellow solid (1.33 g).

$^1$HNMR (d$_6$-DMSO): δ 5.90 (s, 2H), 6.64 (s, 1H), 6.67 (d, 1H), 7.10 (d, 1H), 7.51 (s, 1H), 7.56 (d, 1H), 7.92 (d, 1H), 10.62 (s, 1H).

LCMS Rt=1.14 min MS m/z 255 [MH]+

Preparation 18

N-(2,4-Dimethoxybenzyl)-5-fluoropyrimidin-2-amine

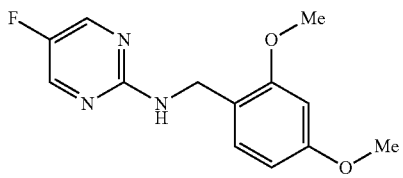 [SMILES: COc1ccc(CNc2ncc(F)cn2)c(OC)c1]

2-Chloro-5-fluoropyrimidine (4.05 g, 30.6 mmol), 2,4-dimethoxybenzylamine (5.0 mL, 31 mmol) and triethylamine (3.72 g, 36.7 mmol) were stirred in ethanol (200 mL) and heated at 50° C. for 48 hours. The cooled reaction mixture was poured into water and extracted with ethyl ether (×2). The combined organic phase was dried over anhydrous magnesium sulfate and concentrated in vacuo. The residue was purified by silica gel column chromatography (hexanes to ethyl acetate gradient elution) then triturated with ethyl ether:hexanes. The solid was collected by filtration and dried in vacuo to afford the title compound as a white solid (4.16 g).

$^1$HNMR (d$_6$-DMSO): δ 3.72 (s, 3H), 3.78 (s, 3H), 4.34 (d, 2H), 6.43 (dd, 1H), 6.53 (d, 1H), 7.04 (d, 1H), 7.46 (t, 1H), 8.33 (d, 1H).

LCMS Rt=1.56 min MS m/z 264 [MH]+

Preparation 19

5-Chloro-N-(2,4-dimethoxybenzyl)-2,4-difluoro-N-(5-fluoropyrimidin-2-yl)benzenesulfonamide

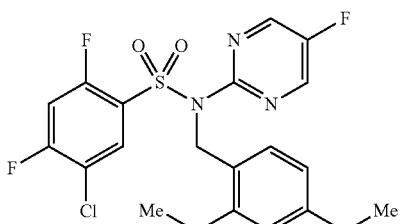

N-(2,4-Dimethoxybenzyl)-5-fluoropyrimidin-2-amine (Preparation 18, 4.00 g, 15.2 mmol) was dissolved in tetrahydrofuran (40 mL) and cooled to −78° C. A 1.0 M solution of lithium hexamethyldisilazide in tetrahydrofuran (17 mL, 17 mmol) was added drop-wise to the solution and the solution was stirred for 30 minutes at −78° C. A solution of 5-chloro-2,4-difluorobenzenesulfonyl chloride (3.42 g, 13.8 mmol) in tetrahydrofuran was added drop-wise to the reaction mixture and it was stirred at −78° C. for 1 h then allowed to warm gradually to ambient temperature. The reaction mixture was stirred for 16 hours then quenched with saturated aqueous ammonium chloride (50 mL). The aqueous phase was extracted with ethyl acetate (×2). The combined organic phase was washed with brine, dried over anhydrous magnesium sulfate, filtered and concentrated in vacuo. The residue was adsorbed onto diatomaceous earth and purified by silica gel column chromatography (hexanes to dichloromethane gradient elution) to afford the title compound as a white solid (1.73 g).

¹HNMR (d₆-DMSO): δ 3.73 (m, 6H), 5.24 (s, 2H), 6.47 (dd, 1H), 6.57 (d, 1H), 7.01 (d, 1H), 7.85 (t, 1H), 8.07 (t, 1H), 8.71 (s, 2H).

LCMS Rt=1.78 min MS m/z 496 [MNa]+

Preparation 20

4-[2-(2-Aminopyridin-4-yl)-4-(trifluoromethyl)phenoxy]-5-chloro-N-(2,4-dimethoxybenzyl)-2-fluoro-N-(5-fluoropyrimidin-2-yl)benzenesulfonamide

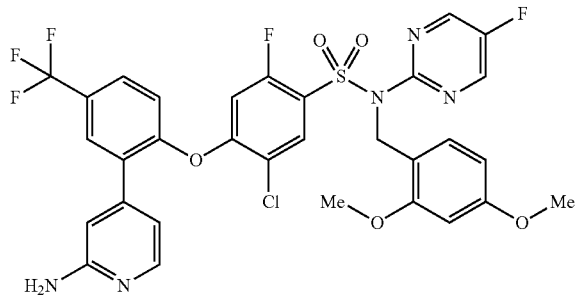 [SMILES: COc1ccc(CN(c2ncc(F)cn2)S(=O)(=O)c2cc(Cl)c(Oc3ccc(C(F)(F)F)cc3-c3ccnc(N)c3)cc2F)c(OC)c1]

2-(2-Aminopyridin-4-yl)-4-(trifluoromethyl)phenol (Preparation 17, 0.93 g, 3.6 mmol) was taken up in dimethylsulfoxide (40 mL) and potassium carbonate (0.95 g, 6.9 mmol) was added followed by 5-chloro-N-(2,4-dimethoxybenzyl)-2,4-difluoro-N-(5-fluoropyrimidin-2-yl)benzenesulfonamide (Preparation 19, 1.73 g, 3.64 mmol). The reaction mixture was stirred for 18 hours then diluted with water (120 mL) and the solid collected by filtration. The filtrate was extracted with ethyl ether. The solid was dissolved in dichloromethane and combined with the ether extract. The combined organic solution was dried over anhydrous magnesium sulfate, treated with activated carbon and filtered through a pad of diatomaceous earth. The solvent was concentrated in vacuo to give a thick oil. The oil was purified by silica gel column chromatography (0 to 5% methanol in dichloromethane gradient elution) and concentrated in vacuo to afford the title compound as a glass (2.24 g).

LCMS Rt=1.64 min MS m/z 708 [MH]+

Preparation 21

2-(2-Aminopyridin-4-yl)-4-fluorophenol

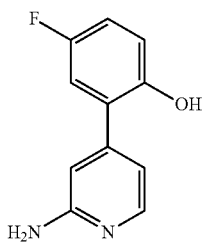 [SMILES: Nc1cc(-c2cc(F)ccc2O)ccn1]

Argon was bubbled through a suspension of (5-fluoro-2-hydroxyphenyl)boronic acid (55.0 mg, 0.35 mmol), 4-bromopyridin-2-amine (67.1 mg, 0.39 mmol) and sodium carbonate (0.15 g, 1.4 mmol) in 1,4-dioxane (0.9 mL) and water (0.3 mL) for 5 minutes then tetrakis(triphenylphosphine)palladium(0) (41 mg, 0.04 mmol) was added. The resulting mixture was heated at 85° C. for 22 hours then cooled to ambient temperature and diluted with ethyl acetate and water. The layers were separated and the aqueous layer extracted with ethyl acetate. The combined organic extracts were dried over anhydrous sodium sulfate, filtered, and concentrated in vacuo. The residue was purified by automated silica gel flash chromatography (0% to 100% ethyl acetate in hexanes gradient elution) to afford the title compound as a light tan solid (62 mg).

¹HNMR (d₆-DMSO): δ 5.92 (br s, 2H), 6.69 (m, 2H), 6.89-7.18 (m, 3H), 7.94 (d, 1H), 9.76 (s, 1H).

LCMS Rt=0.31 min MS m/z 205 [MH]+

Preparation 22

4-Bromo-3-nitro-1-(tetrahydro-2H-pyran-2-yl)-1H-pyrazole or 4-Bromo-5-nitro-1-(tetrahydro-2H-pyran-2-yl)-1H-pyrazole

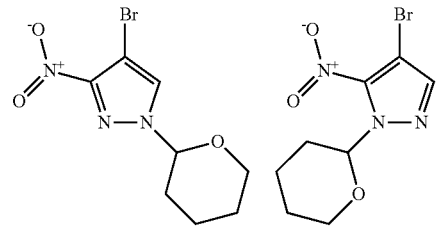

First Batch

A suspension of 4-bromo-3-nitro-1H-pyrazole (54.31 g, 282.9 mmol) and trifluoroacetic acid (1.05 mL, 13.6 mmol) in toluene (450 mL, 4200 mmol) was heated at 80° C. Dihydropyran (28.5 mL, 312 mmol) was added slowly over 10 minutes to see if an exotherm occurred. No temperature increase was noted during addition of the dihydropyran. The temperature was increased to just below reflux. The solid slowly dissolved. After 23 hours, the reaction mixture was cooled to ambient temperature and concentrated in vacuo. The residue was washed successively with water, 1N aqueous potassium hydrogen sulfate, 1N aqueous sodium bicarbonate, and brine. The organic layer was dried over anhydrous magnesium sulfate, filtered, and concentrated in vacuo to afford a brown oil. The residue was dissolved in methylene chloride, diluted with hexanes, and concentrated in vacuo to afford a brown solid. The solid was dissolved in hot ethyl acetate and cooled to −10° C. in a freezer. After 18 hours, the resulting solid was collected by filtration to afford the title compound as a crystalline solid (45.74 g).

Second Batch

A 5 L 3-neck flask equipped with a mechanical stirrer, temperature probe, and an addition funnel was charged with 4-bromo-3-nitro-1H-pyrazole (136 g, 708 mmol), toluene (1.1 L), and trifluoroacetic acid (2.63 mL, 34.1 mmol). The reaction mixture was heated to 80° C. Dihydropyran (71.4 mL, 783 mmol) was added over 30 minutes via addition funnel. The reaction mixture became more homogeneous over the course of addition of dihydropyran. The addition funnel was replaced with a condenser, and the reaction mixture heated to 110° C. After 21 hours, the reaction mixture was cooled and concentrated in vacuo to a brown solid. The residue was taken up in ethyl acetate (1.5 L) and washed successively with water (200 mL), saturated aqueous sodium bicarbonate (200 mL), and brine (2×200 mL). The organic layer was dried over anhydrous magnesium sulfate and concentrated in vacuo to half the initial volume. The solution was treated with activated charcoal, filtered through diatomaceous earth, and concentrated in vacuo to half the volume with the bath temperature set at 40° C. The solution was transferred to a 1 L Erlenmeyer flask, seeded with crystals from the first batch, and cooled in the freezer. After 45 hours, the crystals were collected by filtration, washed sparingly with cold ethyl acetate, and dried in vacuo to afford the title compound as a light tan powder (73.03 g).

The filtrate was concentrated to ~100 mL, transferred to a 500 mL Erlenmeyer flask, seeded with crystals from the first batch, and cooled in the freezer. After 3 days, the crystals were collected by filtration, washed sparingly with ethyl acetate then hexanes, and dried in vacuo to afford a second crop of the title compound as a light tan powder (67.4 g).

Only one regioisomeric product was obtained as indicated by $^1$HNMR analysis, but the regioisomer was not determined.

$^1$HNMR ($d_6$-DMSO): δ 1.56 (m, 2H), 1.68 (m, 1H), 1.99 (m, 3H), 3.67 (m, 1H), 3.92 (m, 1H), 5.56 (m, 1H), 8.55 (s, 1H).

LCMS Rt=1.51 min

Preparation 23

[2-Hydroxy-5-(trifluoromethoxy)phenyl]boronic acid

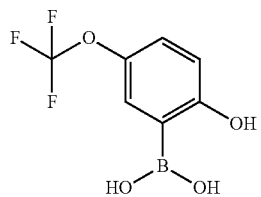 [SMILES: OB(O)c1cc(OC(F)(F)F)ccc1O]

A suspension of 2-methoxy-5-(trifluoromethoxy)phenylboronic acid (23.0 g, 97.5 mmol) in dichloromethane (140 mL) was cooled to 0° C. and boron tribromide (9.4 mL, 10 mmol) was added drop-wise over 30 min. After stirring for 3 hours, additional boron tribromide (2 mL) was added. The reaction mixture was poured into ice water and stirred for 20 min. The dichloromethane was removed in vacuo and the white solid collected by filtration and washed with water before drying in vacuo to afford the title compound (20.8 g).

$^1$HNMR ($d_4$-Methanol): δ 6.78 (d, 1H), 7.11 (d, 1H), 7.40 (br s, 1H).

LCMS Rt=1.67 min MS m/z 221 [M-H]−

Preparation 24

2-[3-Nitro-1-(tetrahydro-2H-pyran-2-yl)-1H-pyrazol-4-yl]-4-(trifluoromethoxy)phenol

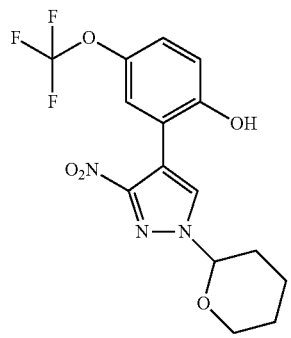 [SMILES: O=[N+]([O-])c1nn(C2CCCCO2)cc1-c1cc(OC(F)(F)F)ccc1O]

To a solution of 2-hydroxy-5-(trifluoromethoxy)phenylboronic acid (Preparation 23, 20.5 g, 92.4 mmol) and 4-bromo-3-nitro-1-(tetrahydro-2H-pyran-2-yl)-1H-pyrazole or 4-bromo-5-nitro-1-(tetrahydro-2H-pyran-2-yl)-1H-pyrazole (Preparation 22, 22.7 g, 82.2 mmol) in 1,2-dimethoxyethane (300 mL) and 2 M potassium carbonate in water (117 mL, 212 mmol) was added tetrakis(triphenylphosphine)palladium(0) (5.0 g, 4.3 mmol). The solution was sparged with argon (×3) and heated at 80° C. for 8 hours. The reaction mixture was cooled to ambient temperature and the layers separated. The aqueous phase was washed with ethyl acetate (×2). The combined organic phase was dried over anhydrous magnesium sulfate and concentrated in vacuo. The residue was purified by silica gel column chromatography (0 to 30% ethyl acetate in hexanes gradient elution) and concentrated in vacuo. Excess hexanes was added to the residue and the resulting solid was collected by filtration and dried in vacuo to afford the title compound as off white crystals (19.5 g).

$^1$H NMR (300 MHz, $d_6$-DMSO): δ 1.46-1.78 (m, 3H), 1.87-2.20 (m, 3H), 3.69 (m, 1H), 3.97 (d, 1H), 5.56 (d, 1H), 6.93 (d, 1H), 7.22 (d, 1H), 7.31 (s, 1H), 8.33 (s, 1H), 10.19 (br s, 1H).

LCMS Rt=1.77 min MS m/z 372 [M-H]−

Preparation 25 tert-Butyl[(5-chloro-2-fluoro-4-{2-[3-nitro-1-(tetrahydro-2H-pyran-2-yl)-1H-pyrazol-4-yl]-4-(trifluoromethoxy)phenoxy}phenyl)sulfonyl]1,3-thiazol-4-ylcarbamate

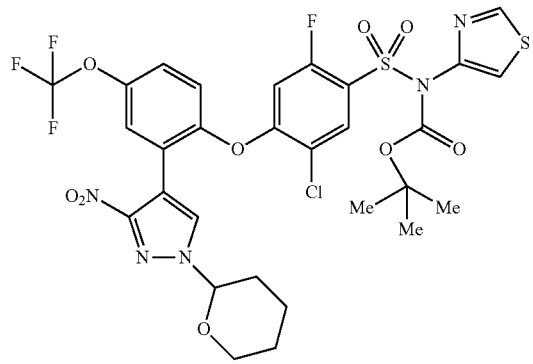 [SMILES: CC(C)(C)OC(=O)N(c1cscn1)S(=O)(=O)c1cc(Cl)c(Oc2ccc(OC(F)(F)F)cc2-c2cn(C3CCCCO3)nc2[N+](=O)[O-])cc1F]

To a solution of 2-[3-nitro-1-(tetrahydro-2H-pyran-2-yl)-1H-pyrazol-4-yl]-4-(trifluoromethoxy)phenol (Preparation 24, 2.00 g, 5.36 mmol) and tert-butyl[(5-chloro-2,4-difluorophenyl)sulfonyl]1,3-thiazol-4-ylcarbamate (Preparation 4, 2.20 g, 5.36 mmol) in dimethylsulfoxide (30 mL) was added potassium carbonate (1.5 g, 11 mmol). The reaction mixture was stirred for 18 hours at ambient temperature. The reaction mixture was then diluted with water and extracted with ethyl acetate (×3). The combined organic phase was washed with water (×2) then dried over anhydrous magnesium sulfate and concentrated in vacuo. The residue was triturated with ether and the solid collected by filtration and dried in vacuo to afford the title compound with a 5% de-boc impurity (3.70 g). The compound was used without further purification in the next step.

LCMS Rt=1.68 min MS m/z 764 [MH]+

Preparation 26

3-Chloro-N-(2,4-dimethoxybenzyl)-4-fluoro-N-1,3,4-thiadiazol-2-ylbenzenesulfonamide

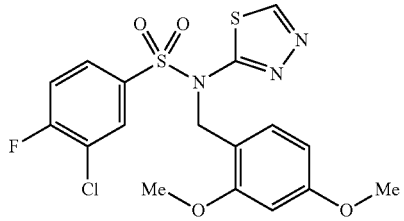 [SMILES: COc1ccc(CN(c2nncs2)S(=O)(=O)c2ccc(F)c(Cl)c2)c(OC)c1]

The title compound was prepared according to procedure used in Preparation 6, Method 1, using 3-chloro-4-fluorobenzene-1-sulfonyl chloride (0.91 g) to obtain the title compound as a white solid (1.3 g).

LCMS Rt=1.70 min MS m/z 466 [MNa]+

Preparation 27

4-Fluoro-2-[3-nitro-1-(tetrahydro-2H-pyran-2-yl)-1H-pyrazol-4-yl]phenol

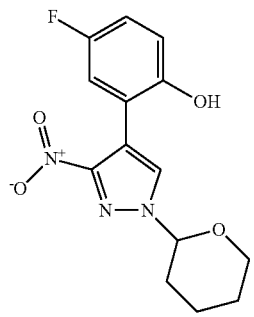

To a mixture of (5-fluoro-2-hydroxyphenyl)boronic acid (225 mg, 1.44 mmol) and 4-bromo-3-nitro-1-(tetrahydro-2H-pyran-2-yl)-1H-pyrazole or 4-bromo-5-nitro-1-(tetrahydro-2H-pyran-2-yl)-1H-pyrazole (Preparation 22, 498 mg, 1.80 mmol) in 1,2-dimethoxyethane (4.5 mL) and 2 M solution of potassium carbonate in water (2.0 mL) was added tetrakis(triphenylphosphine)palladium(0) (86.71 mg, 0.08 mmol). The mixture was sparged with argon (×3) and heated at 80° C. for 4 hours. Additional 5-fluoro-2-hydroxyphenyl)boronic acid (56 mg) was added and the reaction mixture stirred with heating for 18 additional hours. The reaction mixture was cooled to ambient temperature, diluted with ethyl acetate, and filtered through diatomaceous earth. The layers were separated and the organic layer washed with water and brine, dried over anhydrous magnesium sulfate, filtered, then concentrated in vacuo. The residue was purified by automated silica gel flash chromatography (100% hexanes to 50% ethyl acetate in hexanes gradient elution) to afford the title compound as a light yellow solid (275 mg, 62%).

LCMS Rt=1.50 min MS m/z 306 [M-H]−

Preparation 28 tert-Butyl[(5-chloro-2-fluoro-4-{4-fluoro-2-[3-nitro-1-(tetrahydro-2H-pyran-2-yl)-1H-pyrazol-4-yl]phenoxy}phenyl)sulfonyl]1,3-thiazol-4-carbamate

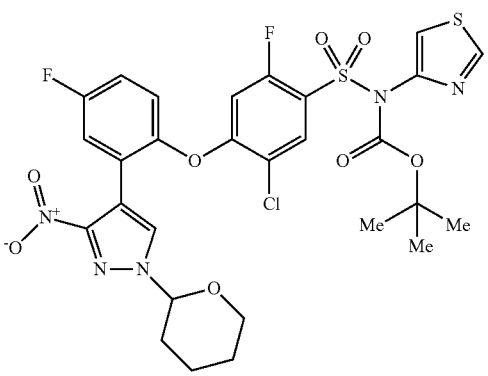

A mixture of 4-fluoro-2-[3-nitro-1-(tetrahydro-2H-pyran-2-yl)-1H-pyrazol-4-yl]phenol (Preparation 27, 50.5 mg, 0.16 mmol) and potassium carbonate (45.4 mg, 0.33 mmol) in dimethylsulfoxide (1.0 mL) was stirred for 10 minutes at ambient temperature. tert-Butyl[(5-chloro-2,4-difluorophenyl)sulfonyl]1,3-thiazol-4-ylcarbamate (Preparation 4, 67.5 mg, 0.16 mmol) was added, and the reaction mixture was stirred at ambient temperature. After 24 hours, the reaction mixture was diluted with ethyl acetate, washed with water and brine, dried over anhydrous sodium sulfate, filtered, and concentrated in vacuo. The residue was purified by automated silica gel flash chromatography (10% to 100% ethyl acetate in hexanes gradient elution) to afford the title compound as a white solid (85 mg, 76%).

LCMS Rt=2.02 min MS m/z 720 [MNa]+

Preparation 29

2-Iodo-4-(trifluoromethoxy)phenol

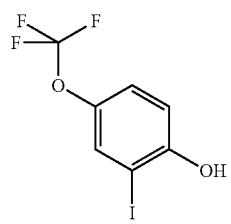 [SMILES: Oc1ccc(OC(F)(F)F)cc1I]

To a suspension of N-iodosuccinimide (6.95 g, 31 mmol) in glacial acetic acid (2 ml) was added 4-trifluoromethoxy phenol (4.0 ml, 31 mmol) and, after 5 minutes, concentrated sulphuric acid (0.5 ml, 9 mmol). The pale brown suspension was stirred at ambient temperature under nitrogen for 48 hours before diluting with water and extracting with dichloromethane. The organic extract was washed with water, saturated aqueous sodium thiosulfate solution and water, dried over anhydrous magnesium sulfate and decolorizing charcoal added. The resulting suspension was left to stand for 30 minutes before filtering through a short pad of silica gel eluting with dichloromethane. The solvent was concentrated in vacuo to afford the title compound as an oil (1.18 g, 12%).

$^1$HNMR (CDCl$_3$): δ 5.49 (br s, 1H), 6.99 (d, 1H), 7.15 (dd, 1H), 7.55 (d, 1H).

LCMS Rt=1.51 min MS m/z 303 [MH]−

Preparation 30

2-Pyridazin-4-yl-4-(trifluoromethoxy)phenol

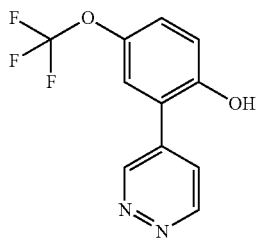 [SMILES: Oc1ccc(OC(F)(F)F)cc1-c1ccnnc1]

2-Iodo-4-(trifluoromethoxy)phenol (Preparation 29, 3.30 g, 9.99 mmol) and 4-(tributylstannyl)pyridazine (4.06 g, 11.0 mmol) were taken up in dimethylformamide (40 mL). Cesium fluoride (3.03 g, 20.0 mmol) was added followed by tetrakis(triphenylphosphine)palladium(0) (1.2 g, 1.0 mmol) and copper(I) iodide (380 mg, 2.0 mmol). The reaction mixture was evacuated and purged with argon (×5) then heated at 45° C. After 2 hours the reaction mixture was cooled and diluted with ethyl acetate and water. The mixture was filtered through a pad of diatomaceous earth and washed with ethyl acetate. The aqueous phase was separated and back extracted with ethyl acetate. The combined organic phase was concentrated in vacuo. The residue was purified by silica gel column chromatography (0% to 10% methanol in dichloromethane gradient elution) then triturated with ethyl ether. The solid was collected by filtration and dried in vacuo to afford the title compound product as a yellow solid (1.18 g, 46%).

$^1$HNMR ($d_6$-DMSO): δ 7.09 (d, 1H), 7.34 (m, 1H), 7.56 (d, 1H), 7.92 (dd, 1H), 9.26 (dd, 1H), 9.49 (dd, 1H), 10.64 (s, 1H).

LCMS Rt=1.62 min MS m/z 257 [MH]+

Preparation 31 tert-Butyl 3-hydrazinoazetidine-1-carboxylate

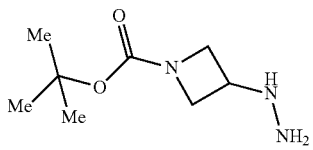

tert-Butyl 3-iodoazetidine-1-carboxylate (142 g, 0.50 mol) and hydrazine hydrate (245.2 mL, 5.02 mol) were mixed in ethanol (284 mL) and the reaction mixture was heated to 85° C. for 48 hours under nitrogen. The reaction mixture was cooled and the ethanol was removed in vacuo. The residue was partitioned between water (200 mL) and dichloromethane (300 mL), the water layer was re-extracted with dichloromethane (2×200 mL), the combined organics were dried over anhydrous magnesium sulphate, filtered and concentrated in vacuo to afford the title compound as a colourless oil (88.37 g). This compound was used immediately in the next step without purification.

$^1$HNMR (CDCl$_3$): δ 1.44 (s, 9H), 3.05 (br s, 3H), 3.65-3.76 (m, 3H), 4.00-4.07 (m, 2H).

Preparation 32

1-[2-Hydroxy-5-(trifluoromethyl)phenyl]ethanone

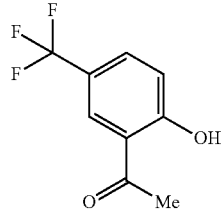

To a stirred solution of 1-[2-methoxy-5-(trifluoromethyl)phenyl]ethanone (35 g, 0.16 mol) in dry dichloromethane (400 mL) at 0° C. was added solid tetrabutylammonium iodide (2.96 g, 0.008 mol) followed by boron tribromide (33.96 mL, 0.35 mol) drop-wise. After addition, the reaction mixture was stirred at ambient temperature for 1.5 hours. The reaction mixture was cooled to 0° C. and quenched with ice. The mixture was extracted with diethyl ether (1 L). The organic layer was washed with water (2 L) and then saturated aqueous sodium chloride (1 L). After concentration of the organic layer at ambient temperature in vacuo, the crude product was purified by silica gel column chromatography (2% diethyl ether in hexane elution) to afford the title compound as a colourless oil (11.5 g, 35%).

$^1$HNMR (CDCl$_3$): δ 2.68 (s, 3H), 7.07 (d, 1H), 7.69 (d, 1H), 7.98 (s, 1H), 12.53 (s, 1H).

GCMS Rt=5.59 min MS m/z 203 [M-H]

Preparation 33

(2E)-3-(Dimethylamino)-1-[2-hydroxy-5-(trifluoromethyl)phenyl]prop-2-en-1-one

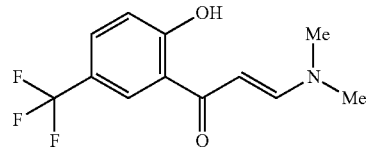 [SMILES: CN(C)/C=C/C(=O)c1cc(C(F)(F)F)ccc1O]

1-[2-Hydroxy-5-(trifluoromethyl)phenyl]ethanone, (Preparation 32, 7.0 g, 0.034 mol) was taken in dimethylformamide dimethylacetal (18.2 mL, 0.14 mol) at ambient temperature and then heated at 110° C. for 30 minutes. The reaction mixture was concentrated in vacuo and the crude product was crystallised from 2-propanol to afford the title compound as bright yellow solid (6.4 g, 73%). $^1$HNMR (CDCl$_3$): δ 3.02 (s, 3H) 3.22 (s, 3H), 5.72 (d, 1H), 6.99 (d, 1H), 7.55 (d 1H), 7.89-7.94 (m, 2H), 14.45 (s, 1H).

LCMS Rt=1.61 min MS m/z 260 [MH]+

Preparation 34 tert-Butyl 3-[5-(5-trifluoromethyl-2-hydroxyphenyl)-1H-pyrazol-1-yl]azetidine-1-carboxylate

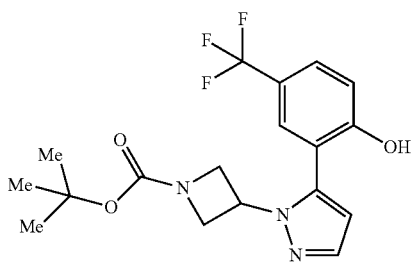 [SMILES: CC(C)(C)OC(=O)N1CC(n2nccc2-c2cc(C(F)(F)F)ccc2O)C1]

To a stirred solution of crude tert-butyl 3-hydrazinoazetidine-1-carboxylate, (Preparation 31, 5.7 g, 0.03 mol) in ethanol (66 mL) at 0° C. was added acetic acid (6.6 mL) dropwise. Then (2E)-3-(dimethylamino)-1-[2-hydroxy-5-(trifluoromethyl)phenyl]prop-2-en-1-one, (Preparation 33, 6.4 g, 24.7 mmol) was added portionwise and allowed to stir at ambient temperature for 20 hours. The reaction mixture was concentrated in vacuo and neutralised with aqueous sodium bicarbonate solution. The mixture was extracted with ethyl acetate (150 mL). The combined organic layer was washed with water (100 mL), saturated aqueous sodium chloride solution (50 mL) and dried over anhydrous sodium sulphate. After concentration of organic layer in vacuo, the crude product was washed with 20% v/v ethyl acetate in hexane to afford the title compound as a white solid (7.4 g, 64%)

$^1$HNMR (CDCl$_3$): δ 1.45 (s, 9H), 4.27-4.37 (m, 3H), 4.70 (br s, 1H), 4.79-4.83 (m, 1H), 6.25 (s, 1H), 7.16 (d, 1H), 7.46 (s, 1H), 7.55 (d, 1H), 7.66 (s, 1H), 9.64 (s, 1H).

HPLC Purity: 99.84%

LCMS Rt=3.52 min MS m/z 384 [MH]+

Preparation 35 tert-Butyl 3-{5-[5-trifluoromethyl-2-(2-chloro-4-{[(2,4-dimethoxybenzyl)(1,3,4-thiadiazol-5-yl)amino]sulfonyl}-5-fluorophenoxy)phenyl]-1H-pyrazol-1-yl}azetidine-1-carboxylate

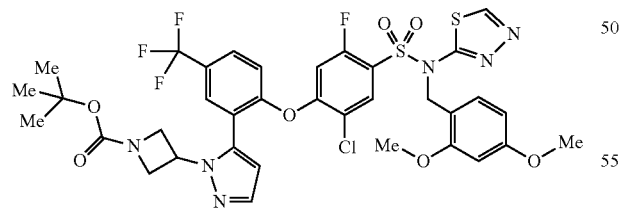

tert-Butyl 3-[5-(5-trifluoromethyl-2-hydroxyphenyl)-1H-pyrazol-1-yl]azetidine-1-carboxylate (Preparation 34, 400 mg, 1.04 mmol) and potassium carbonate (450 mg, 3.26 mmol) were combined in dimethylsulfoxide (5 mL). To this slurry was added 5-chloro-N-(2,4-dimethoxybenzyl)-2,4-difluoro-N-1,3,4-thiadiazol-2-ylbenzenesulfonamide (Preparation 6, 482 mg, 1.04 mmol) and stirred at ambient temperature for 3 hours. tert-Butylmethyl ether (30 mL) and water (30 mL) were added and the layers separated. The organic layer was washed with water (2×30 mL), then dried over anhydrous magnesium sulphate, filtered and concentrated in vacuo to give a foam. The foam was purified by silica gel flash column chromatography (20% to 40% ethyl acetate in heptane gradient elution) to afford the title compound as a colourless foam (600 mg, 70%).

$^1$HNMR (CDCl$_3$): δ 1.45 (s, 9H), 3.68 (s, 3H), 3.76 (s, 3H), 4.28 (m, 2H), 4.44 (m, 2H), 4.91 (m, 1H), 5.32 (s, 2H), 6.22 (s, 1H), 6.30 (s, 1H), 6.34 (m, 1H), 6.40 (m, 1H), 7.08 (d, 1H), 7.26 (m, 1H), 7.66 (m, 2H), 7.79 (m, 2H), 8.84 (s, 1H).

LCMS Rt=1.90 min MS m/z 847 [M$^{35}$ClNa]+

Preparation 36

4-Fluoro-5-iodobenzenesulfonyl chloride

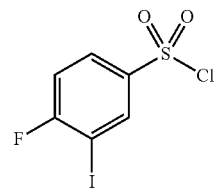 [SMILES: O=S(=O)(Cl)c1ccc(F)c(I)c1]

2-Fluoroiodobenzene (0.58 mL, 5.0 mmol) was added dropwise to chlorosulfonic acid (1.66 mL, 25 mmol) at 0° C. The reaction mixture was allowed to warm to ambient temperature and stirred for 2 hours. The reaction mixture was poured into ice and the mixture was extracted with dichloromethane (3×30 mL). The combined organic layer was dried over magnesium sulfate and concentrated in vacuo to obtain a crude residue. The crude residue was dissolved in heptane (100 mL) and the suspension was filtered. The filtrate was concentrated in vacuo to afford the title compound.

$^1$HNMR (d$_6$-DMSO): δ 7.17-7.23 (m, 1H), 7.58-7.64 (m, 1H), 7.97 (dd, 1H).

Preparation 37

N-(2,4-Dimethoxybenzyl)-4-fluoro-5-iodo-N-1,2,4-thiadiazol-5-ylbenzenesulfonamide

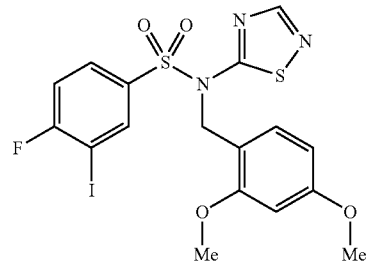 [SMILES: COc1ccc(CN(c2ncns2)S(=O)(=O)c2ccc(F)c(I)c2)c(OC)c1]

The title compound was prepared according to Preparation 6 using (2,4-dimethoxy-benzyl)[1,2,4]thiadiazol-5-yl-amine/N-(2,4-dimethoxybenzyl)-1,2,4-thiadiazol-5-amine and 4-fluoro-5-iodobenzenesulfonyl chloride (Preparation 36).

$^1$HNMR (d$_6$-DMSO): δ 3.60 (s, 3H), 3.65 (s, 3H), 5.20 (s, 2H), 6.40 (m, 2H), 7.00 (m, 1H), 7.40 (m, 1H), 7.90 (m, 1H), 8.00 (m, 1H), 8.40 (s, 1H).

LCMS Rt=1.82 min MS m/z 558 [MNa]+

Preparation 38

N-(2,4-Dimethoxybenzyl)-3-iodo-4-[2-pyridazin-4-yl-4-(trifluoromethyl)phenoxy]-N-1,2,4-thiadiazol-5-ylbenzenesulfonamide

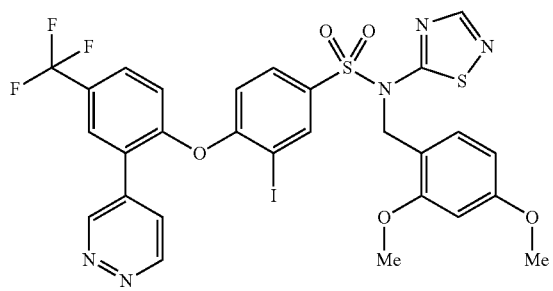 [SMILES: COc1ccc(CN(c2ncns2)S(=O)(=O)c2ccc(Oc3ccc(C(F)(F)F)cc3-c3ccnnc3)c(I)c2)c(OC)c1]

The title compound was prepared according to Preparation 35 at 60° C. over 4 days using 2-pyridazin-4-yl-4-(trifluoromethyl)phenol (Preparation 30) and N-(2,4-dimethoxybenzyl)-4-fluoro-5-iodo-N-1,2,4-thiadiazol-5-ylbenzenesulfonamide (Preparation 37) to give the product (420 mg, 43%).

$^1$HNMR (d$_6$-DMSO): δ 3.60 (s, 3H), 3.65 (s, 3H), 5.2 (s, 2H), 6.4 (m, 2H), 6.95 (m, 1H), 7.15 (m, 2H), 7.80 (m, 1H), 7.85 (m, 1H), 7.90 (m, 1H), 8.00 (m, 1H), 8.10 (m, 1H), 8.40 (s, 1H), 9.3 (m, 1H), 9.55 (m, 1H).

LCMS Rt=3.61 min MS m/z 756 [MH]+

Preparation 39

3-Cyano-4-fluoro-N-(1,2,4-thiadiazol-5-yl)benzenesulfonamide

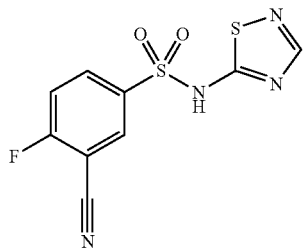 [SMILES: N#Cc1cc(S(=O)(=O)Nc2ncns2)ccc1F]

Sodium hydroxide (5.08 g, 130 mmol) was dissolved in water (60 mL) and 1,4-dioxane (300 mL). 1,2,4-Thiadiazol-5-amine (10 g, 100 mmol) was added and the reaction mixture was stirred for 5 minutes. 3-Cyano-4-fluorobenzene-1-sulfonyl chloride (8.25 g, 38 mmol) was added and the reaction mixture was allowed to stir for 3 hours at 20° C. After this time, the reaction mixture was poured into 1N aqueous hydrogen chloride solution (150 mL). This solution was extracted with ethyl acetate (3×50 mL). The combined organics were dried over sodium sulfate, filtered and concentrated in vacuo to afford the title compound as a brown solid (13 g, 69%).

$^1$HNMR (d$_6$-DMSO): δ 7.71 (m, 1H), 8.19 (m, 1H), 8.39 (dd, 1H), 8.54 (s, 1H)

LCMS Rt=1.22 min MS m/z 283 [MH]−

Preparation 40

5-Hydroxy-4-[2-methoxy-5-(trifluoromethyl)phenyl]-5-methylfuran-2(5H)-one

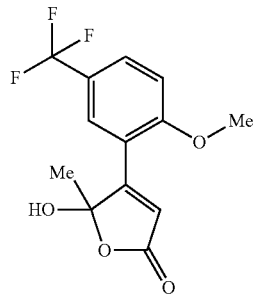 [SMILES: COc1ccc(C(F)(F)F)cc1C1=CC(=O)OC1(C)O]

5-(Trifluoromethyl)-2-methoxyphenylacetone (2800 mg, 12 mmol) was mixed with glyoxylic acid (2.7 mL 18 mmol) and stirred at 100° C. for 16 hours. The reaction mixture was then concentrated in vacuo and azeotroped with toluene to afford the title compound (3.5 g).

LCMS Rt=3.20 min MS m/z 287 [MH]−

Preparation 41

5-[2-Methoxy-5-(trifluoromethyl)phenyl]-6-methylpyridazin-3(2H)-one

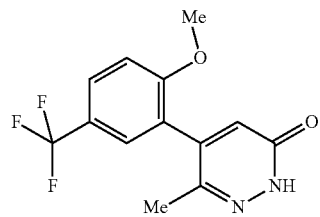 [SMILES: COc1ccc(C(F)(F)F)cc1-c1cc(=O)[nH]nc1C]

5-Hydroxy-4-[2-methoxy-5-(trifluoromethyl)phenyl]-5-methylfuran-2(5H)-one (Preparation 40, 3 g, 10 mmol) was dissolved in ethanol and cooled to 0° C. Hydrazine monohydrate (1.0 mL, 20 mmol) was added drop-wise to this solution, then the reaction mixture was heated to 90° C. for 16 hours. The reaction mixture was then concentrated in vacuo, azeotoped with toluene and the crude material purified by silica gel column chromatography (ISCO™ Companion, 50% ethyl acetate in heptane elution) to afford the title compound as an off-white solid (1.05 g).

$^1$HNMR (CDCl$_3$): δ 2.07 (s, 3H), 3.86 (s, 3H), 6.76 (s, 1H) 7.05 (d, 1H) 7.38 (s, 1H) 7.69 (d, 1H), 10.82 (s, 1H).

Preparation 42

6-Chloro-4-[2-methoxy-5-(trifluoromethyl)phenyl]-3-methylpyridazine

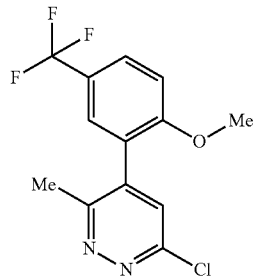 [SMILES: COc1ccc(C(F)(F)F)cc1-c1cc(Cl)nnc1C]

5-[2-Methoxy-5-(trifluoromethyl)phenyl]-6-methylpyridazin-3(2H)-one (Preparation 41, 1.1 g, 39 mmol) and phosphorus oxychloride (20 mL) were heated to 100° C. for 3 hours. The reaction mixture was then cooled to 0° C. and poured onto ice before being neutralised with sodium bicarbonate. The mixture was extracted with dichloromethane (3×100 mL) and the combined organic layer washed with water (50 mL) then saturated aqueous sodium chloride solution (50 mL). The organics were dried over sodium sulfate, filtered and concentrated in vacuo. The crude material was purified by silica gel column chromatography (20% ethyl acetate in heptane elution) to afford the title compound as an off-white solid (900 mg).

$^1$HNMR (CDCl$_3$): δ 2.49 (s, 3H), 3.85 (s, 3H), 7.08 (d, 1H) 7.30 (s, 1H) 7.38 (s, 1H) 7.72 (d, 1H).

LCMS Rt=3.45 min MS m/z 303 [MH]+

Preparation 43

4-[2-Methoxy-5-(trifluoromethyl)phenyl]-3-methylpyridazine

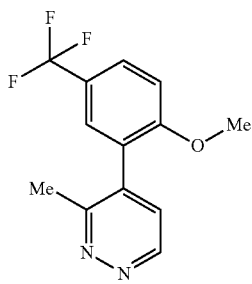 [SMILES: COc1ccc(C(F)(F)F)cc1-c1ccnnc1C]

6-Chloro-4-[2-methoxy-5-(trifluoromethyl)phenyl]-3-methylpyridazine (Preparation 42, 800 mg, 2.6 mmol) was dissolved in methanol (32 mL), the solution was degassed with argon for 15 minutes then palladium on charcoal (160 mg) was added and placed under a balloon of hydrogen gas for 4 hours. The reaction mixture was filtered through diatomaceous earth, washed with methanol (20 mL) and the combined filtrate concentrated in vacuo to afford the title compound as a solid (700 mg).

$^1$HNMR (CDCl$_3$): δ 2.83 (s, 3H), 3.89 (s, 3H), 7.16 (d, 1H) 7.49 (s, 1H) 7.82 (d, 1H) 7.93 (s, 1H) 9.37 (s, 1H).

Preparation 44

2-(3-Methylpyridazin-4-yl)-4-(trifluoromethyl)phenol

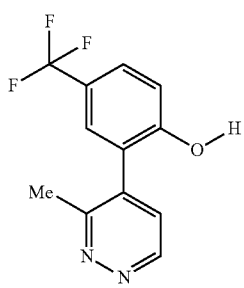 [SMILES: Cc1nnccc1-c1cc(C(F)(F)F)ccc1O]

To a solution of 4-[2-methoxy-5-(trifluoromethyl)phenyl]-3-methylpyridazine (Preparation 43, 650 mg, 2.4 mmol) in N,N-dimethylformamide (18 mL) was added sodium thiomethoxide (850 mg, 12 mmol) and reaction mixture was heated to 70° C. for 4 hours. The reaction mixture was then cooled to 0° C., poured onto ice water (50 mL) and extracted with ethyl acetate (3×100 mL). The combined organics were washed with water (5×100 mL) and saturated aqueous sodium chloride solution (100 mL) then dried over sodium sulfate, filtered and concentrated in vacuo. The crude material was purified by silica gel column chromatography (20% ethyl acetate in heptane elution) to afford the title compound as a yellow solid (325 mg).

$^1$HNMR (CDCl$_3$): δ 2.47 (s, 3H), 7.08 (d, 1H) 7.15 (d, 1H) 7.52 (d, 1H) 7.55 (s, 1H) 9.12 (d, 1H) 10.84 (s, 1H).

LCMS Rt=2.99 min MS m/z 255 [MH]+

Preparation 45 tert-Butyl 1,3-thiazol-4-yl[(2,4,5-trifluorophenyl)sulfonyl]carbamate

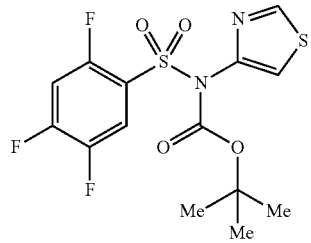 [SMILES: CC(C)(C)OC(=O)N(c1cscn1)S(=O)(=O)c1cc(F)c(F)cc1F]

To a solution of tert-butyl 1,3-thiazol-4-ylcarbamate (Preparation 3, 28.94 g, 145 mmol) in anhydrous tetrahydrofuran (600 mL) at −70° C., under an atmosphere of nitrogen was added lithium 1,1,1,3,3,3-hexamethyldisilazan-2-ide (1 M in tetrahydrofuran, 145 mL, 145 mmol) drop-wise. The reaction mixture was allowed to warm to ambient temperature and stirred for 1 hour before cooling to −70° C. once again. A solution of 2, 4,5-trifluoro benzenesulfonyl chloride (40 g, 173 mmol) in tetrahydrofuran (80 mL) was added drop-wise and then the reaction mixture was slowly warmed to ambient temperature and stirred for 2 hours. The reaction mixture was quenched with saturated aqueous ammonium chloride solution and extracted with ethyl acetate. The organic layer was washed with water and saturated aqueous sodium chloride solution before concentrating in vacuo. The crude residue was purified by silica gel column chromatography (0% to 15% ethyl acetate in hexanes gradient elution) to afford the title compound as white solid (37 g, 64%).

$^1$H NMR (400 MHz, CDCl3): δ 1.35 (s, 9H), 7.07-7.13 (m, 1H), 7.52 (s, 1H), 8.00-8.06 (m, 1H), 8.78 (s, 1H).

LCMS Rt=3.46 minutes. MS m/z 395 [MH]+

Preparation 46

(2,4-dimethoxy-benzyl)-[1,2,4]thiadiazol-5-yl-amine/N-(2,4-dimethoxybenzyl)-1,2,4-thiadiazol-5-amine

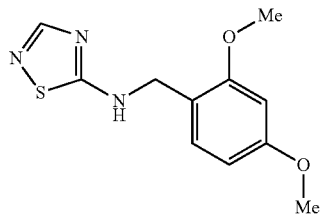 [SMILES: COc1ccc(CNc2ncns2)c(OC)c1]

A mixture of 5-amino-1,2,4-thiadiazole (1.00 g, 9.89 mmol) and 2,4-dimethoxybenzaldehyde (1.81 g, 10.9 mmol) in toluene (30 mL) was refluxed under Dean-Stark conditions for 2 hours. The reaction mixture was concentrated in vacuo, and the resulting residue taken up in methanol (25 mL). Sodium borohydride (600 mg, 15.9 mmol) was added carefully in small portions (vigorous effervescence after each addition) and the reaction was left to stir overnight at ambient temperature. An 2M aqueous solution of hydrogen chloride (1 mL) was added followed by a 2M aqueous solution of sodium hydroxide (10 mL). The mixture was concentrated in vacuo, water (20 mL) added and the mixture extracted with ethyl acetate (2×30 mL). The combined organics were washed with brine (20 mL), dried, and concentrated in vacuo. The residue was purified by silica gel column chromatography (ISCO™ column, 25% to 60% ethyl acetate in heptane gradient elution) to furnish a semi-solid residue. tert-Butylmethyl ether (2-3 mL) was added, followed by heptane (2-3 mL). The resulting solid was collected by filtration, washed with heptane and dried to afford the title compound (1.22 g).

$^1$HNMR ($d_6$-DMSO): δ 3.73 (s, 3H), 3.78 (s, 3H), 4.36 (d, 2H), 6.47 (dd, 1H), 6.56 (d, 1H), 7.15 (d, 1H), 7.88 (s, 1H), 8.65 (br s, 1H)

The ability of the compounds of list (I) to block the Nav1.7 (or SCN9A) channel was measured using the assay described below.

Cell Line Construction and Maintenance

Human Embryonic Kidney (HEK) cells were transfected with an hSCN9A construct using lipofectamine reagent (Invitrogen), using standard techniques. Cells stably expressing the hSCN9A constructs were identified by their resistance to G-418 (400 μg/ml). Clones were screened for expression using the whole-cell voltage-clamp technique.

Cell Culture

HEK cells stably transfected with hSCN9A were maintained in DMEM medium supplemented with 10% heat-inactivated fetal bovine serum and 400 μg/ml G-418 in an incubator at 37° C. with a humidified atmosphere of 10% $CO_2$. For HTS, cells were harvested from flasks by trypsinization and replated in an appropriate multi-well plate (typically 96 or 384 wells/plate) such that confluence would be achieved within 24 hours of plating. For electrophysiological studies, cells were removed from the culture flask by brief trypsinization and re-plated at low density onto glass cover slips. Cells were typically used for electrophysiological experiments within 24 to 72 hours after plating.

Electrophysiological Recording

Cover slips containing HEK cells expressing hSCN9A were placed in a bath on the stage of an inverted microscope and perfused (approximately 1 ml/minutes) with extracellular solution of the following composition: 138 mM NaCl, 2 mM $CaCl_2$, 5.4 mM KCl, 1 mM $MgCl_2$, 10 mM glucose, and 10 mM HEPES, pH 7.4, with NaOH. Pipettes were filled with an intracellular solution of the following composition: 135 mM CsF, 5 mM CsCl, 2 mM $MgCl_2$, 10 mM EGTA, 10 mM HEPES, pH 7.3 with NaOH, and had a resistance of 1 to 2 megaohms. The osmolarity of the extracellular and intracellular solutions was 300 mOsm/kg and 295 mOsm/kg, respectively. All recordings were made at room temperature (22-24° C.) using AXOPATCH 200B amplifiers and PCLAMP software (Axon Instruments, Burlingame, Calif.).

hSCN9A currents in HEK cells were measured using the whole-cell configuration of the patch-clamp technique (Hamill et al., 1981). Uncompensated series resistance was typically 2 to 5 mega ohms and >85% series resistance compensation was routinely achieved. As a result, voltage errors were negligible and no correction was applied. Current records were acquired at 20 to 50 KHz and filtered at 5 to 10 KHz.

HEK cells stably transfected with hSCN9A were viewed under Hoffman contrast optics and placed in front of an array of flow pipes emitting either control or compound-containing extracellular solutions. All compounds were dissolved in dimethyl sulfoxide to make 10 mM stock solutions, which were then diluted into extracellular solution to attain the final concentrations desired. The final concentration of dimethyl sulfoxide (<0.3% dimethyl sulfoxide) was found to have no significant effect on hSCN9A sodium currents. The voltage-dependence of inactivation was determined by applying a series of depolarizing prepulses (8 sec long in 10 mV increments) from a negative holding potential. The voltage was then immediately stepped to 0 mV to assess the magnitude of the sodium current. Currents elicited at 0 mV were plotted as a function of prepulse potential to allow estimation of the voltage at which 50% of the channels were inactivated (midpoint of inactivation or V1/2). Compounds were tested for their ability to inhibit hSCN9A sodium channels by activating the channel with a 20 msec voltage step to 0 mV following an 8 second conditioning prepulse to the empirically determined V1/2. Compound effect (% inhibition) was determined by difference in current amplitude before and after application of test compounds. For ease of comparison, "estimated IC-50" ($EIC_{50}$) values were calculated from single point electrophysiology data by the following equation, (tested concentration, uM)×(100−% inhibition/% inhibition). Inhibition values <20% and >80% were excluded from the calculation.

Electrophysiological assays were conducted with PatchXpress 7000 hardware and associated software (Molecular Devices Corp). All assay buffers and solutions were identical to those used in conventional whole-cell voltage clamp experiments described above. hSCN9A cells were grown as above to 50%-80% confluency and harvested by trypsinization. Trypsinized cells were washed and resuspended in extracellular buffer at a concentration of $1\times10^6$ cells/ml. The onboard liquid handling facility of the PatchXpress was used for dispensing cells and application of test compounds. Determination of the voltage midpoint of inactivation was as described for conventional whole-cell recordings. Cells were then voltage-clamped to the empirically determined V1/2 and current was activated by a 20 msec voltage step to 0 mV.

Electrophysiological assays may also be conducted using the Ionworks Quattro automated electrophysiological platform (Molecular Devices Corp). Intracellular and extracellular solutions were as described above with the following changes, 100 μg/ml amphotericin was added to the intracellular solution to perforate the membrane and allow electrical access to the cells. hSCN9A cells were grown and harvested as for PatchXpress and cells were resuspended in extracellular solution at a concentration of $3\text{-}4\times10^6$ cells/ml. The onboard liquid handling facility of the Ionworks Quattro was used for dispensing cells and application of test compounds. A voltage protocol was then applied that comprised of a voltage step to fully inactivate the sodium channels, followed by a brief hyperpolarized recovery period to allow partial recovery from inactivation for unblocked sodium channels, followed by a test depolarized voltage step to assess magnitude of inhibition by test compound. Compound effect was determined based on current amplitude difference between the pre-compound addition and post-compound addition scans.

Compounds of the Examples were tested in the assay described above using the PatchXpress platform and found to have the Nav1.7 $EIC_{50}$ (uM) values specified in the table below.

| Ex. | $EIC_{50}$ |
|---|---|
| 1 | 0.0067 |
| 2 | 0.005 |
| 3 | 0.018 |
| 4 | 0.0275 |
| 5 | 0.0118 |
| 6 | 0.0085 |
| 7 | 0.0147 |
| 8 | 0.0099 |
| 9 | 0.024 |
| 10 | 0.0108 |
| 11 | 0.0166 |
| 12 | 0.0146 |
| 13 | 0.0011 |
| 14 | 0.0026 |
| 15 | 0.0116 |
| 16 | 0.0032 |
| 17 | 0.01 |

The ability of compounds of list (I) to block the Nav1.5 (or SCN5A) channel can also be measured using an assay analogous to that described above but replacing the SCN9A gene with the SCN5A gene. All other conditions remain the same including the same cell line and conditions for cell growth. The estimated IC50s are determined at the half inactivation for Nav1.5. These results can be compared to the $EIC_{50}$ value at the Nav1.7 channel to determine the selectivity of a given compound for Nav1.7 vs Nav1.5.

The invention claimed is:

1. A compound selected from:
5-Chloro-4-[4-chloro-2-(2-piperazin-1-ylpyrimidin-4-yl)phenoxy]-2-fluoro-N-1,3-thiazol-4-ylbenzenesulfonamide;
5-Chloro-4-[4-chloro-2-(2-piperazin-1-ylpyrimidin-4-yl)phenoxy]-2-fluoro-N-1,3,4-thiadiazol-2-ylbenzenesulfonamide;
5-Chloro-2-fluoro-4-[5-fluoro-2-pyridazin-4-yl-4-(trifluoromethyl)phenoxy]-N-1,3-thiazol-4-ylbenzenesulfonamide;
5-Chloro-2-fluoro-4-[4-fluoro-2-pyridazin-4-yl-5-(trifluoromethyl)phenoxy]-N-1,3-thiazol-4-ylbenzenesulfonamide;
4-[2-(2-Aminopyridin-4-yl)-4-chlorophenoxy]-5-chloro-2-fluoro-N-(5-fluoropyrimidin-2-yl)benzenesulfonamide;
4-[2-(2-Aminopyridin-4-yl)-4-(trifluoromethyl)phenoxy]-5-chloro-2-fluoro-N-(5-fluoropyrimidin-2-yl)benzenesulfonamide;
4-[2-(2-Aminopyridin-4-yl)-4-fluorophenoxy]-5-chloro-2-fluoro-N-1,3-thiazol-4-ylbenzenesulfonamide;
4-[2-(3-Amino-1H-pyrazol-4-yl)-4-(trifluoromethoxy)phenoxy]-5-chloro-2-fluoro-N-1,3-thiazol-4-ylbenzenesulfonamide;
4-[2-(2-Aminopyridin-4-yl)-4-chlorophenoxy]-3-chloro-N-1,3,4-thiadiazol-2-ylbenzenesulfonamide;
4-[2-(2-Aminopyridin-4-yl)-4-chlorophenoxy]-5-chloro-2-fluoro-N-1,3-thiazol-4-ylbenzenesulfonamide;
4-[2-(5-Amino-1H-pyrazol-4-yl)-4-fluorophenoxy]-5-chloro-2-fluoro-N-1,3-thiazol-4-ylbenzenesulfonamide;
5-Chloro-2-fluoro-4-[2-pyridazin-4-yl-4-(trifluoromethoxy)phenoxy]-N-1,3-thiazol-4-ylbenzenesulfonamide;
4-[2-(1-Azetidin-3-yl-1H-pyrazol-5-yl)-5-chloro-2-fluoro-4-(trifluoromethyl)phenoxy]-N-1,3,4-thiadiazol-5-ylbenzenesulfonamide;
3-Cyano-4-[2-(3-methylpyridazin-4-yl)-4-(trifluoromethyl)phenoxy]-N-1,2,4-thiadiazol-5-ylbenzenesulfonamide;
3-Methyl-4-[2-pyridazin-4-yl-4-(trifluoromethyl)phenoxy]-N-1,2,4-thiadiazol-5-ylbenzenesulfonamide;
4-[4-chloro-2-(2-piperazin-1-ylpyrimidin-4-yl)phenoxy]-2,5-difluoro-N-1,3-thiazol-4-ylbenzenesulfonamide;
4-[4-chloro-2-(2-piperazin-1-ylpyridin-4-yl)phenoxy]-2,5-difluoro-N-pyrimidin-2-ylbenzenesulfonamide;
4-[4-chloro-2-(2-piperazin-1-ylpyridin-4-yl)phenoxy]-3-cyano-N-pyrimidin-2-ylbenzenesulfonamide;
4-[4-chloro-2-(2-piperazin-1-ylpyrimidin-4-yl)phenoxy]-3-cyano-N-pyrimidin-2-ylbenzenesulfonamide;
4-[4-chloro-2-(2-piperazin-1-ylpyrimidin-4-yl)phenoxy]-2,5-difluoro-N-pyrimidin-2-ylbenzenesulfonamide;
or a pharmaceutically acceptable salt thereof.

2. A pharmaceutical composition comprising a compound as defined in claim 1 with one or more pharmaceutically acceptable excipients.

3. A pharmaceutical composition according to claim 2 including one or more additional therapeutic agents.

4. A method of treating pain in a mammal, comprising administering to said mammal a therapeutically effective amount of a compound as defined in claim 1.

5. The method according to claim 4 in which said pain is selected from the group consisting of neuropathic pain, nociceptive pain and inflammatory pain.

6. A compound of the formula:

or a pharmaceutically acceptable salt thereof.

7. A method of treating pain in a mammal, comprising administering to said mammal a therapeutically effective amount of a compound as defined in claim 6.

8. The method according to claim 7 in which said pain is selected from the group consisting of neuropathic pain, nociceptive pain and inflammatory pain.

9. A pharmaceutical composition comprising a compound as defined in claim 6 with one or more pharmaceutically acceptable excipients.

10. A pharmaceutical composition according to claim 9 including one or more additional therapeutic agents.

* * * * *